(12) United States Patent
Kohno et al.

(10) Patent No.: US 6,509,002 B1
(45) Date of Patent: *Jan. 21, 2003

(54) DIAGNOSTIC AGENT FOR DIABETES

(75) Inventors: Tadashi Kohno, Kanagawa (JP); Isaburo Hosoi, Saitama (JP); Junko Ohshima, Kanagawa (JP); Asuka Ito, Kanagawa (JP); Kunihiko Shibata, Chiba (JP)

(73) Assignee: Tokyo Gas Company Limited, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/176,246

(22) Filed: Oct. 21, 1998

(30) Foreign Application Priority Data

| Oct. 21, 1997 | (JP) | ................................................. 9-288526 |
| Oct. 21, 1997 | (JP) | ................................................. 9-288629 |
| Nov. 14, 1997 | (JP) | ................................................. 9-313077 |
| Nov. 14, 1997 | (JP) | ................................................. 9-313763 |
| Nov. 21, 1997 | (JP) | ................................................. 9-320805 |
| Dec. 11, 1997 | (JP) | ................................................. 9-341154 |
| Jan. 16, 1998 | (JP) | ................................................. 10-006410 |
| Feb. 5, 1998 | (JP) | ................................................. 10-024613 |
| Feb. 5, 1998 | (JP) | ................................................. 10-024614 |

(51) Int. Cl.$^7$ .......................... A61K 51/00; A61M 36/14
(52) U.S. Cl. ..................... 424/1.81; 424/1.11; 424/1.65; 424/9.1
(58) Field of Search ............................ 424/1.11, 1.65, 424/1.81, 9.1, 9.2; 562/589

(56) References Cited

U.S. PATENT DOCUMENTS

| 4,298,347 A | * | 11/1981 | Walsh ........................ 23/230 B |
| 5,834,466 A | * | 11/1998 | Ramasamy et al. ....... 514/227.5 |
| 6,071,245 A | * | 6/2000 | Kohno et al. ................ 600/532 |

FOREIGN PATENT DOCUMENTS

| EP | 0503832 A1 | 9/1992 | .............. C12P/1/00 |
| EP | 0826377 A1 | 3/1998 | .......... A61K/49/00 |
| EP | 0908187 A1 | 4/1999 | .......... A61K/51/12 |
| JP | 2680861 | 10/1988 | .......... A61K/49/00 |
| WO | WO9205270 | 4/1992 | ........... C12P/19/02 |
| WO | WO9201937 | 2/1999 | .......... G01N/33/60 |
| WO | WO9956790 | 11/1999 | .......... A61K/51/00 |

OTHER PUBLICATIONS

Dox et al, The Harper Collins Illustrated Medical Dictionary, p. 237, 1993.*

Kosugi et al, J. Biological Chemistry, vol. 261, No. 9, pp. 3952–3957 "Pathways of Acetone's Metabolism in the Rat", Mar. 1986.*

Peroni et al, Metabolism, vol. 46, No. 11, pp. 1358–1363 "Glucose Production and Gluconeogenesis in Post–absorptive and Starved Normal and Streptzotocin—Diabetic Rats" Nov. 1997.*

Cohen, Biochemistry, vol. 26, No. 2, pp. 563–572, "$^{13}$C and $^{31}$P NMR Study of Gluconeogenesis: Utilization of $^{13}$C–Labeled Substrates by Refused Liver from Streptozocin–Diabetic and Untreated Rats" 1987.*

Mathew van Holde, *Biochemistry*, 1990, The Benjamin/Cummings Publishing Company, Inc. pp. 446–450 & 543–544, 1990.*

Goromaru et al (1994), Biol. Pharm. Bull., vol. 17, No. 1, pp. 156–159.*

Hiele et al (1988), Biomedical and Environmental Mass Spectrometry, vol. 16, pp. 133–135.*

Normand et al (1992), Am. J. clin. Nutr., vol. 55, pp. 430–435.*

Berry et al (1995), Biochemical and Molecular Medicine, vol. 56, pp. 158–165.*

D. Rating, et al., *Breath tests: concepts, applications and limitations*, European Journal of Pediatrics, vol. 156, Suppl. 1, pp. S18–S23, (1997).

(List continued on next page.)

*Primary Examiner*—Dameron L. Jones
(74) *Attorney, Agent, or Firm*—Davidson, Davidson & Kappel, LLC

(57) ABSTRACT

The present invention relates to a diagnostic agent for diabetes, comprising a compound labelled with $^{13}$C at least at one specific position selected from the group consisting of the following (a) to (g):

(a) galactose, fructose or xylose labelled with $^{13}$C at least atone specific position, or a starch composed of glucose units labelled with $^{13}$C at least at one specific position;

(b) an amino acid labelled with $^{13}$C at least at one specific position;

(c) lactic acid or citric acid labelled with $^{13}$C at least at one specific position;

(d) a fatty acid labelled with $^{13}$C at least at one specific position;

(e) a glyceride labelled with $^{13}$C at least at one specific position;

(f) glycerol labelled with $^{13}$C at least at one specific position; and (g) aminopyrin of which the dimethylamino group at position 4 is labelled with $^{13}$C, phenacetin of which the ethoxy group is labelled with $^{13}$C at position 1, or methacetin of which the methoxy group is labelled with $^{13}$C.

According to the present invention, there is provided a diagnostic agent for diabetes which does not impose a heavy physical burden on a subject, can give accurate test results immediately and can be used safely without side effects. The diagnostic agent of the invention makes it possible to discriminate patients with diabetes from normal subjects even under circumstances where patients are easily missed.

2 Claims, 33 Drawing Sheets

OTHER PUBLICATIONS

Helge, et al., *Carbon–13 dioxide breath tests in normal and diabetic children following ingestion of 13C–glucose*, In: Baillie TA, ed. *Stable isotopes*. Baltimore, Univ Park Press, (1978). QV 20.5 l61s 1978. (no abstract available).

Tanis, et al., *Human liver glycogen metabolism assessed with a 13C–enriched diet and a 13C02 breath test*, European Journal of Clinical Investigation, vol. 28, No. 6, pp. 466–474 (1998) XP–002120263 (abstract).

M. Hirai, et al., *The Breath Test Using Pure [$1-^{13}C$] Glucose: A New Simple Method of Evaluating the Glucose Oxidation Capacity*, Diabetologia, vol. 40, p. a278, (1997) XP–000865704, XP–002120262 (abstract).

Gerard T. Berry, et al., *In Vivo Oxidation of [$^{13}C$] Galactose in Patients with Galactose–1–Phosphate Uridyltransferase Deficiency*, Biochemical and Molecular Medicine, vol. 56, pp. 158–165, (1995) XP–002089101.

* cited by examiner

DIAGNOSTIC AGENT FOR DIABETES

BACKGROUND OF THE INVENTION

1. Field of the Invention

The present invention relates to a diagnostic agent for diabetes. More specifically, the present invention relates to a diagnostic agent for diabetes which comprises a compound labelled with $^{13}C$ at least at one specific position.

2. Description of the Prior Art

Test methods generally used in the primary screening in diagnosis of diabetes are urine sugar test and fasting blood sugar level test. These tests are simple and high in specificity, but are low in sensitivity and give negative results for patients with light diabetes. Thus, 70% or more patients are missed and these tests are considered inadequate as screening tests for diabetes (Sekikawa et al., Medical Practice 10:63, 1933). On the other hand, the glucose tolerance test used for diagnosis of diabetes causes side effects due to administration of a large amount of glucose, and this test requires restraint of a subject for several hours and repeated collection of blood, imposing a heavy physical burden on the subject. Further, the procedures of this test are troublesome. Therefore, this test is actually impossible to carry out as a screening test for diabetes. Recently, blood HbA1C and fructosamine tests, which reflect the average blood sugar level of a subject for a certain period in the past, have been introduced as screening tests for diabetes in some facilities. Under the existing circumstances, however, even these tests cannot be said to be adequate in sensitivity and specificity for light diabetes, and there remains the problem of difference in measurement results among facilities.

Blood sugar level, HbA1C and fructosamine tests have been used widely for management of outpatients with diabetes and evaluation of therapeutic effects. However, since blood sugar levels will drop at the time of fasting in the case of light diabetes, they cannot be a criterion for the evaluation. HbA1C and fructosamine tests have, in addition to the above-described problems, the following problem: the results of these tests cannot be known until the next visit to the hospital, so instructions are given to the patient on the basis of the past test results.

Under such circumstances, there is a demand for development of a test method for diagnosis of diabetes, management of patients with diabetes and evaluation of therapeutic effects, which method is effective even for patients with light diabetes, does not impose a heavy burden on subjects, and gives results immediately and accurately.

OBJECTS AND SUMMARY OF THE INVENTION

It is an object of the present invention to provide a diagnostic agent for diabetes which is effective even for patients with light diabetes, does not impose a heavy burden on subjects, and can give accurate test results immediately.

As a result of their eager researches toward the solution of the above problems, the present inventors have found that it is possible to diagnose diabetes accurately by administering to a subject a compound labelled with $^{13}C$ at least at one specific position and measuring the degree of increase of $^{13}C$ levels in the exhaled $CO_2$. Thus, the present invention has been achieved.

The present invention relates to a diagnostic agent for diabetes, comprising a compound labelled with $^{13}C$ at least at one specific position selected from the group consisting of the following (a) to (g):

(a) galactose, fructose or xylose labelled with $^{13}C$ at least at one specific position, or a starch composed of glucose units labelled with $^{13}C$ at least at one specific position;

(b) an amino acid labelled with $^{13}C$ at least at one specific position;

(c) lactic acid or citric acid labelled with $^{13}C$ at least at one specific position;

(d) a fatty acid labelled with $^{13}C$ at least at one specific position;

(e) a glyceride labelled with $^{13}C$ at least at one specific position;

(f) glycerol labelled with $^{13}C$ at least at one specific position; and (g) aminopyrin of which the dimethylamino group at position 4 is labelled with $^{13}C$, phenacetin of which the ethoxy group is labelled with $^{13}C$ at position 1, or methacetin of which the methoxy group is labelled with $^{13}C$.

DETAILED DESCRIPTION OF THE INVENTION

Figure 1:
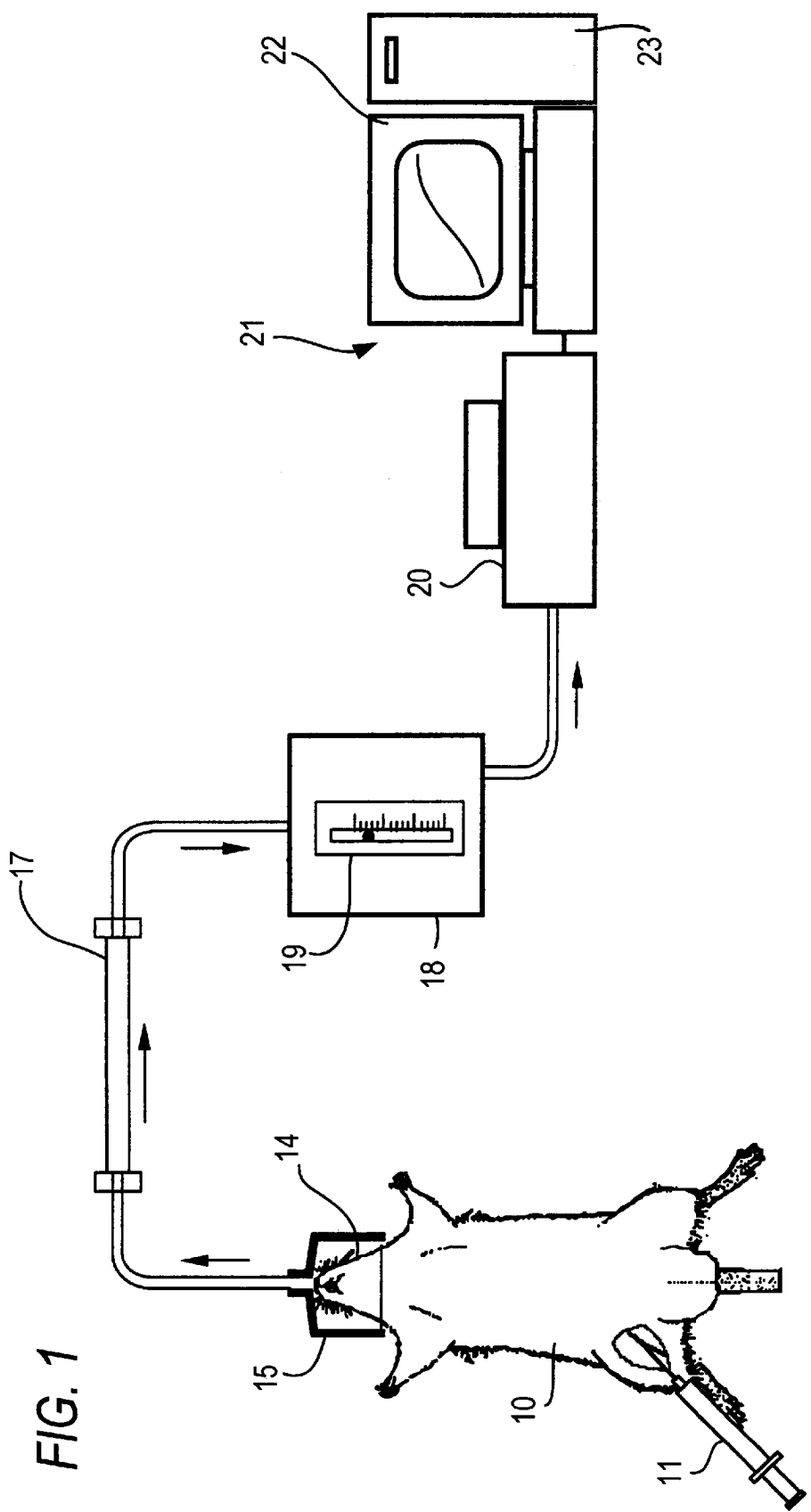
FIG. 1 shows a method of sampling an exhalation from a rat.

Hereinbelow, the present invention will be described in detail.

In the diagnostic agent of the present invention, galactose, fructose or xylose labelled with $^{13}$C at least at one specific position or a starch composed of glucose units labelled with $^{13}$C at least at one specific position may be used. The position of the labelling is not particularly limited.

Alternatively, an aliphatic amino acid, aromatic amino acid, sulfur-containing amino acid, heterocyclic amino acid, acidic amino acid or basic amino acid labelled with $^{13}$C at least at one specific position may be used in the diagnostic agent of the present invention. The position of the labelling is not particularly limited.

Preferable examples of the aliphatic amino acid include, but are not limited to, glycine, alanine, serine, threonine, valine, leucine and isoleucine. Preferable examples of the aromatic amino acid include, but are not limited to, phenylalanine and tyrosine. Preferable examples of the sulfur-containing amino acid include, but are not limited to, cysteine, cystine and methionine. Preferable examples of the heterocyclic amino acid include, but are not limited to, tryptophan, proline and histidine. Preferable examples of the acidic amino acid include, but are not limited to, aspartic acid, asparagine, glutamic acid and glutamine. Preferable examples of the basic amino acid include, but are not limited to, arginine, lysine and ornithine.

Alternatively, lactic acid or citric acid labelled with $^{13}$C at least at one specific position may be used in the diagnostic agent of the present invention. The position of the labelling is not particularly limited.

Alternatively, a fatty acid labelled with $^{13}$C at least at one specific position may be used in the diagnostic agent of the present invention. The position of the labelling is not particularly limited.

Preferable examples of the fatty acid include, but are not limited to, acetic acid, octanoic acid, palmitic acid, oleic acid, linolic acid and linolenic acid.

Alternatively, a glyceride labelled with $^{13}$C at least at one specific position may be used in the diagnostic agent of the present invention. The position of the labelling is not particularly limited.

Preferable examples of the glyceride include, but are not limited to, trioctanoin, tripalmitin, triolein and triacetin.

Alternatively, glycerol labelled with $^{13}$C at least at one specific position may be used in the diagnostic agent of the present invention. The position of the labelling is not particularly limited.

Alternatively, aminopyrin of which the dimethylamino group at position 4 is labelled with $^{13}$C (N,N-dimethyl-$^{13}$C-aminopyrin), phenacetin of which the ethoxy group is labelled with $^{13}$C at position 1 (ethoxy-1-$^{13}$C-phenacetin), or methacetin of which the methoxy group is labelled with $^{13}$C (methoxy-$^{13}$C-methacetin) may be used in the diagnostic agent of the present invention. The structures of N,N-dimethyl-$^{13}$C-aminopyrin, ethoxy-1-$^{13}$C-phenacetin and methoxy-$^{13}$C-methacetin are shown in the following formulas (I) to (III), respectively.

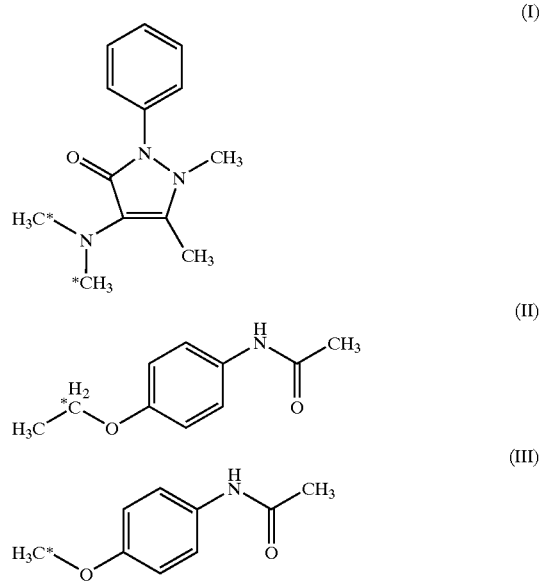

Any of the above-mentioned compounds used in the present invention is contained in foods, or the safety thereof as a medicine has been established. Further, unlike radioisotopes, $^{13}$C is a stable isotope, and thus there is no danger of exposure to radiation. Accordingly, the diagnostic agent of the invention has no problem in its safety.

The test using the diagnostic agent of the invention is a breath test in which the agent is administered to a subject once or continuously and then the increase of $^{13}$C levels in the exhaled $CO_2$ is measured. Specifically, $^{13}$C levels in the exhaled $CO_2$ after administration of the agent are measured, followed by evaluation of diabetes from data on the degree of increase of $^{13}$C levels in the exhaled $CO_2$ ($\Delta^{13}C$ (‰)) at predetermined intervals (e.g., 5 min, 10 min, 15 min) after the administration, total amount of $^{13}CO_2$ exhalation for a predetermined time after administration of the reagent, or data on the time course (slope at the start, change in the slope, peak time, etc.) of the degree of increase of $^{13}$C levels in the exhaled $CO_2$ ($\Delta^{13}C$ (‰)) for a predetermined time period after the administration. The results of this breath test are useful by themselves, but it is more preferable to use these results in combination with blood sugar levels, HbA1C values and fructosamine values for diagnosis.

$^{13}C$ levels in exhaled $CO_2$ can be determined using gas chromatography mass spectrometry (GC-MS), infrared spectrophotometry, mass spectrometry, photoelectric acoustic spectrophotometry and NMR (nuclear magnetic resonance).

The diagnostic agent of the invention for diabetes can be formulated into pharmaceutical preparations such as parenteral agents (tablets, capsules, powder, granules, liquid, etc.), injections and the like, depending on the administration route, by using the above-described compound labelled with $^{13}C$ at least at one specific position alone or mixing it with fillers or carriers. The fillers or carriers may be any of those conventionally used in this field as long as they are pharmaceutically acceptable. The type and composition of such fillers or carriers are altered appropriately according to the route and method of administration. For example, water is used as a liquid carrier. As solid carriers, cellulose derivatives such as hydroxypropyl cellulose and organic acid salts such as magnesium stearate are used. Water, physiological saline and various buffer solutions are generally desirable in the preparation of injections. Such preparations may be lyophilized for use as oral agents, or the lyophilized preparations may be dissolved in suitable injection solvents e.g. liquids for intravenous administration (such as sterilized water, physiological saline, electrolyte, etc.) just before use.

The content of the labelled compound in the pharmaceutical preparation varies depending to the type of the preparation, and is usually in the range of 1 to 100% by weight, preferably 50 to 100% by weight. In the case of injections, for example, the labelled compound is added usually in an amount of 1 to 40% by weight. In the case of capsules, tablets, granules and powder, the content of the labelled compound is in the range from about 10 to 100% by weight, preferably 50 to 100% by weight, with the remainder being carriers.

The diagnostic agent of the invention for diabetes should be administered at such a dosage that enables the confirmation of an increase of $^{13}CO_2$ in an exhalation after administration of the diagnostic agent. Depending on the age and weight of the patient and the object of the test, the dosage for each administration ranges from 1 to 1000 mg/kg body weight in the case of an adult.

EFFECT OF THE INVENTION

According to the present invention, there is provided a diagnostic agent for diabetes which does not impose a heavy physical burden on a subject, can give accurate test results immediately and can be used safely without side effects. With the diagnostic agent of the invention, patients with light diabetes who exhibit normal blood sugar levels at the time of fasting can be screened. Thus, the diagnostic agent of the invention makes it possible to discriminate patients with diabetes from normal subjects even under circumstances where patients are easily missed. Further, the diagnostic agent of the invention is useful for management of out patient with diabetes and evaluation of therapeutic effects.

PREFERRED EMBODIMENTS OF THE INVENTION

Hereinbelow, the present invention will be described more specifically below with reference to the following Examples. However, the scope of the present invention is not limited to these Examples.

The $^{13}C$ purity at the position of labelling in each of the compounds used in the present invention is 99% or more. Unless otherwise indicated, all the reagents used were guaranteed reagents.

EXAMPLE 1

Method of Breath Test (1) Preparation of Rats with Light Diabetes

As test animals, male Sprague-Dawley strain (SD) neonatal rats were purchased from Nippon Charles River K. K. together with their lactating rats. They were bred at 23±2° C. under 55±10% humidity before use.

Insulin secretion-deficient type diabetes was generated by administering streptozotocin (STZ) to neonatal rats ("Saibokogaku (Cell Engineering)", Extra Issue, medical Experiment Manual Series, Strategy for Study of Diabetes, edited by Susumu Seino and Yoshikazu Oka, published by Shujunsha Co., Japan). STZ was subcutaneously administered to 2-day-old rats at a dose of 90 mg/kg. The STZ had been dissolved in a citrate buffer (pH 4.5) and was administered within 5 min after the dissolution. Two days after the administration, blood was collected by cardiac puncture, and the casual blood sugar level of each rat was measured with Terumo Mediace (blood sugar measurement set). Those rats showing a casual blood sugar level of 275 mg/dl or above were selected. In these rats, their casual blood sugar levels begin to rise at 5 weeks after the administration STZ. At 7 weeks after the administration, almost all rats show a high casual blood level. However, their fasting blood sugar levels increase only slightly and remain at almost normal levels.

According to the standards stipulated by the Japan Diabetes Society (1982), those individuals with a fasting blood sugar level (in venous whole blood) of 120 mg/kg or more are regarded as having diabetes ("Tonyobyo Kensa Manyuaru (Diabetes Test Manual)", edited by Yukio Shigeta, published by Nanko-Do Co., Japan). Then, those rats with a fasting blood sugar level of less than 120 mg/dl (and with a casual blood sugar level of 250 mg/dl or more) which are not regarded as having diabetes in a fasting blood sugar level test were selected from the above-described rats with insulin secretion-deficient type diabetes and used as a model of light diabetes.

(2) $^{13}C$ Breath Test

Breath tests were carried out according to the method as described in (2)-1 or (2)-2 below on diabetic rats prepared in (1) above (8–10-week-old) and normal rats (8–10-week-old).

(2)1 Intravenous Administration

Rats 10 fasted overnight were anesthetized by intraperitoneal administration of Nembutal (50 mg/kg) and fixed on an operation table (FIG. 1). A blood sample was collected from the tail vein, and its sugar level was determined using Terumo Mediace (blood sugar measurement set). The head 14 was covered with a cap 15 for sucking the exhalation. A specific amount of the labelled compound was administered 11 from the femoral vein. The exhalation was sucked with a stroke pump 18 (variable stroke pump VS-500; Shibata Scientific Technology) at a rate of 100 ml/min and introduced directly into a flow cell in $^{13}CO_2$ Analyzer EX-130S (Japan Spectroscopic Co., Ltd.) 20. A Perma Pure Drier 17 (MD-050-12P; Perma Pure Inc.) was located between the cap 15 and the stroke pump 18 to remove moisture in the exhalation (FIG. 1).

The data output from the $^{13}CO_2$ analyzer 20 were incorporated into a personal computer 21 (Apple Power Macintosh 8500) after AD conversion. Using the data processing software Lab VIEW (National Instruments), data on ten points at every 100 msec were added up and averaged at intervals of 5 sec and then converted into $^{13}C$ atom %, $\Delta^{13}C$ (‰) and $CO_2$ gas concentration (%), to thereby perform a continuous measurement $^{13}C$ breath test. The converted data were displayed on the screen 22 in real time and then stored in the hard disk 23. During the measurement, the rectum temperature in the rat 10 was monitored and maintained at 37±0.5° C. using a body temperature controller for small animals (TR-100; Fine Science Tools Inc.). The $CO_2$ gas concentration in the sucked exhalation was maintained at 3±0.5%.

$\Delta^{13}C$ (‰) was calculated from the $^{13}C$ level in exhaled $CO_2$ at each time point ($^{13}C$ t min) and the $^{13}C$ level in standard $CO_2$ gas ($^{13}C$ std) using the following formula:

$$\Delta^{13}C (‰) = [(^{13}C \text{ t min} - ^{13}C \text{ 0 min})/^{13}C \text{ std}] \times 1000$$

(2)-2 Oral Administration

Rats 10 fasted overnight were fixed individually in a rat holder of a microwave irradiation apparatus without anesthesia. A blood sample was collected from the tail vein, and its sugar level was determined using Terumo Mediace (blood sugar measurement set). The exhalation was sucked with a stroke pump 18 (variable stroke pump VS-500; Shibata Scientific Technology) at a rate of 100–300 ml/min and introduced directly into a flow cell in $^{13}CO_2$ Analyzer EX-130S (Japan Spectroscopic Co., Ltd.) 20. A Perma Pure Drier (MD-050–12P; Perma Pure Inc.) was located between the rat holder and the stroke pump 18 to remove moisture in the exhalation (FIG. 1). When the $CO_2$ gas concentration was stabilized, the rat 10 was once released from the rat holder, and then a specific amount of the labelled compound was administered into its stomach using a sound for oral administration.

The data output from the $^{13}CO_2$ analyzer 20 were incorporated into a personal computer 21 (Apple Power Macintosh 8500) after AD conversion. Using the data processing software Lab VIEW (National Instruments), data on ten points at every 100 msec were added up and averaged at intervals of 5 sec and then converted into $^{13}C$ atom %, $\Delta^{13}C$ (‰) and $CO_2$ gas concentration (%), to thereby perform a continuous measurement $^{13}C$ breath test. The converted data were displayed on the screen 22 in real time and then stored in the hard disk 23. The $C)_2$ gas concentration in the sucked exhalation was maintained at 3±0.5%.

$\Delta^{13}C$ (‰) was calculated by the formula described above.

(EXAMPLE 2)

1-$^{13}C$-Galactose Breath Test

1-$^{13}C$-galactose (purchased from ICON) dissolved in physiological saline was administered to normal rats (9-week-old; fasting blood sugar level 74.8±5.1 mg/dl; n=4) and diabetic rats (9-week-old; casual blood sugar level 423.3±87.5 mg/dl; fasting blood sugar level 94±118.5 mg/dl; n=4) from the femoral vein at a dose of 100 mg/kg. Then, degrees of increase of $^{13}C$ levels in exhaled $CO_2$ ($\Delta^{13}C$ (‰)) were measured according to the method described in Example 1.

Figure 2:
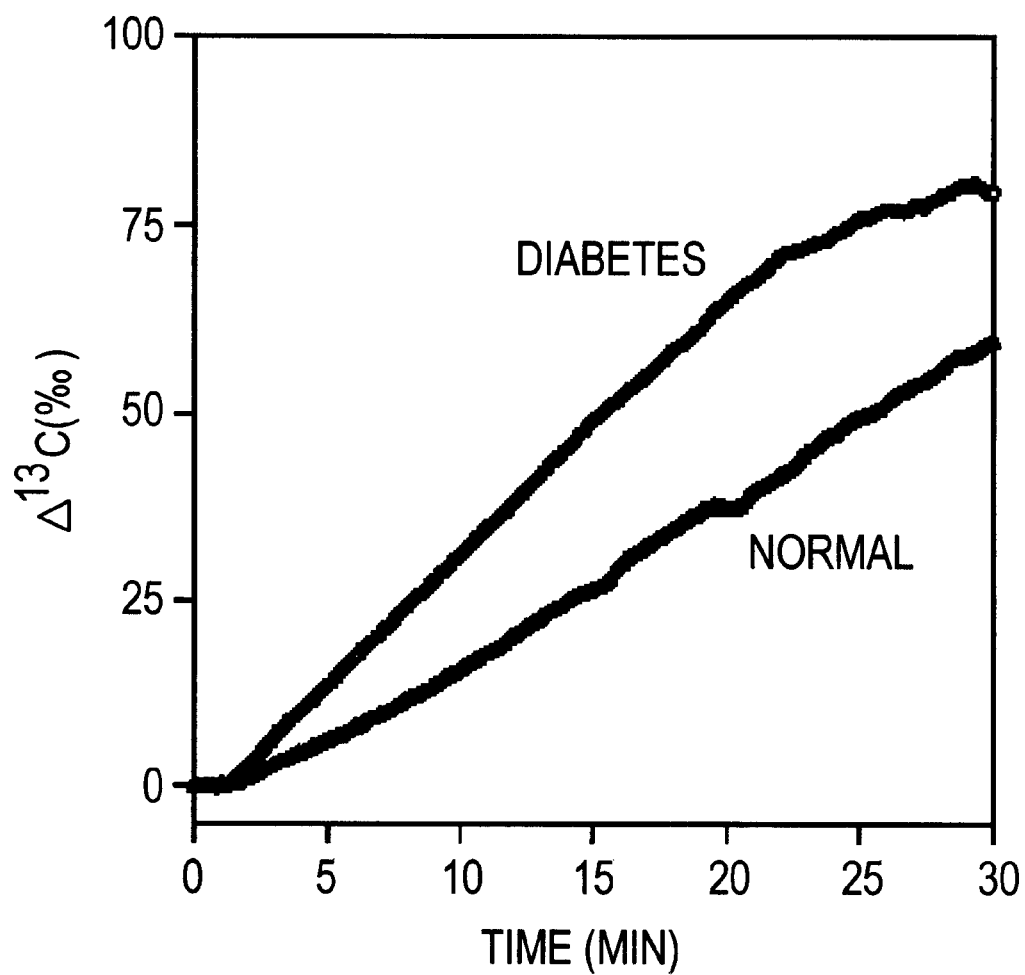
FIG. 2 shows the increase of $^{13}CO_2$ in exhalation after administration of 1-$^{13}C$-galactose.

$\Delta^{13}C$ values (‰) continued increasing up to 30 min after the administration of 1-$^{13}C$-galactose in both the normal and the diabetic rats (FIG. 2).

The $\Delta^{13}C$ value (‰) at 20 min after the administration was 64.90±5.75‰ in the diabetic rats, while the corresponding value was 37.31±3.37‰ in the normal rats. Thus, the value in the diabetic rats was very significantly (p<0.01 (ANOVA with Fischer LSD)) higher than that in the normal rats.

The slope from 5 to 15 min after the administration was 35.53±4.34‰/10 min in the diabetic rats, while the corresponding slope was 20.59±2.26‰/10 min in the normal rats. Thus, the slope in the diabetic rats was very significantly (p<0.01 (ANOVA with Fischer LSD)) greater than that in the normal rats.

Accordingly, it is possible to diagnose diabetes from the $\Delta^{13}C$ value (‰) at a specific time after administration of 1-$^{13}C$-galactose or the slope of increase of $\Delta^{13}C$ values (‰) after the administration. With this test, it is possible to diagnose even light diabetes which shows a normal blood sugar level at the time of fasting.

EXAMPLE 3

2-$^{13}C$-Galactose Breath Test

2-$^{13}C$-galactose (purchased from ICON) dissolved in physiological saline was administered to normal rats (9-week-old; fasting blood sugar level 63.8±13.4 mg/dl; n=4) and diabetic rats (9-week-old; casual blood sugar level 371.5±63.4 mg/dl; fasting blood sugar level 86.5±22.6 mg/dl; n=4) from the femoral vein at a dose of 100 mg/kg. Then, degrees of increase of $^{13}C$ levels in exhaled $CO_2$ ($\Delta^{13}C$ (‰)) were measured according to the method described in Example 1.

Figure 3:
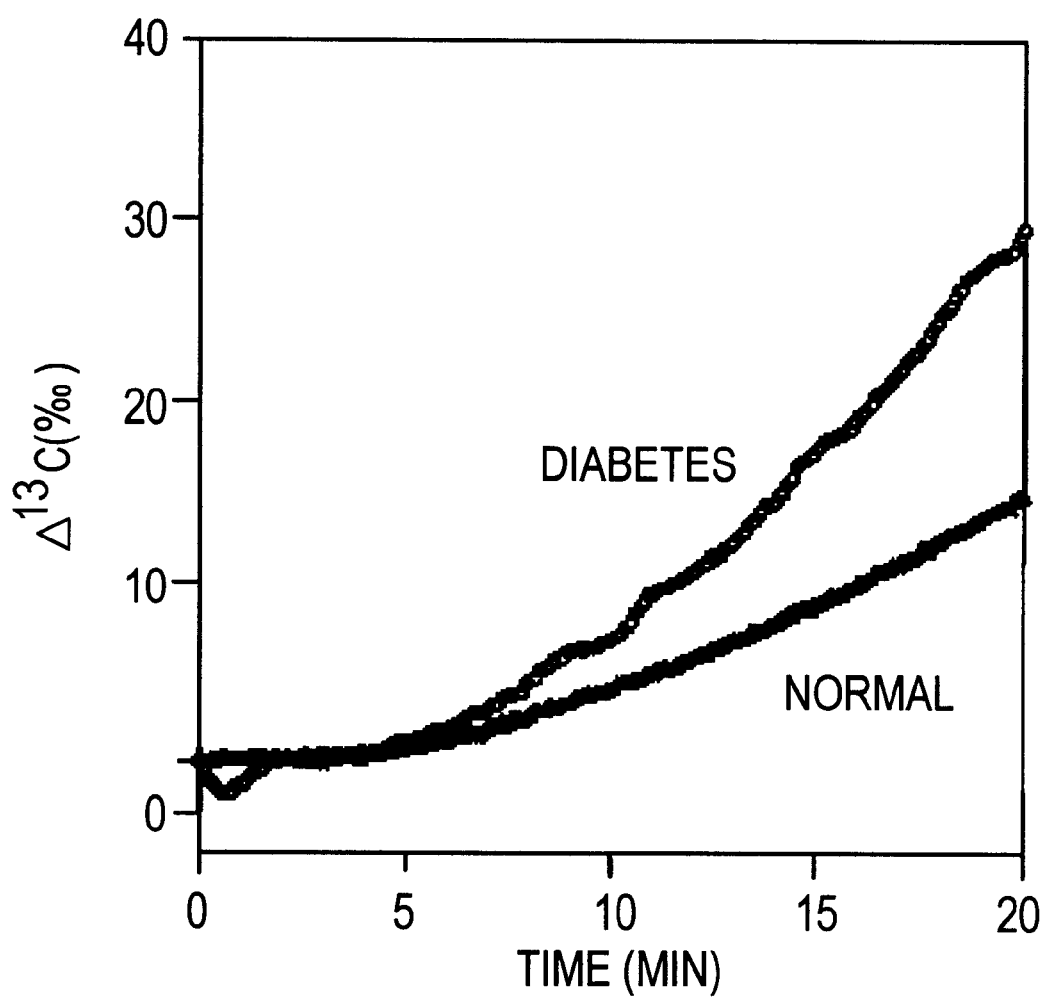
FIG. 3 shows the increase of $^{13}CO_2$ in exhalation after administration of 2-$^{13}C$-galactose.

$\Delta^{13}C$ values (‰) continued increasing up to 20 min after the administration of 2-$^{13}C$-galactose in both the normal and the diabetic rats (FIG. 3).

The $\Delta^{13}C$ value (‰) at 20 min after the administration was 29.68±8.55‰ in the diabetic rats, while the corresponding value was 15.00±1.63‰ in the normal rats. Thus, the value in the diabetic rats was significantly (p<0.05 (ANOVA with Fischer LSD)) higher than that in the normal rats.

Accordingly, it is possible to diagnose diabetes from the $\Delta^{13}C$ value (‰) at a specific time after administration of 2-$^{13}C$-galactose. With this test, it is possible to diagnose even light diabetes which shows a normal blood sugar level at the time of fasting.

EXAMPLE 4

1-$^{13}C$-Fructose Breath Test

1-$^{13}C$-fructose (purchased from ICON) dissolved in physiological saline was administered to normal rats (8-week-old; fasting blood sugar level 75.3±4.1 mg/dl; n=4) and diabetic rats (8-week-old; casual blood sugar level 498.5±75.1 mg/dl; fasting blood sugar level 99.3±11.8 mg/dl; n=4) from the femoral vein at a dose of 100 mg/kg. Then, degrees of increase of $^{13}C$ levels in exhaled $CO_2$ ($\Delta^{13}C$ (‰)) were measured according to the method described in Example 1.

Figure 4:
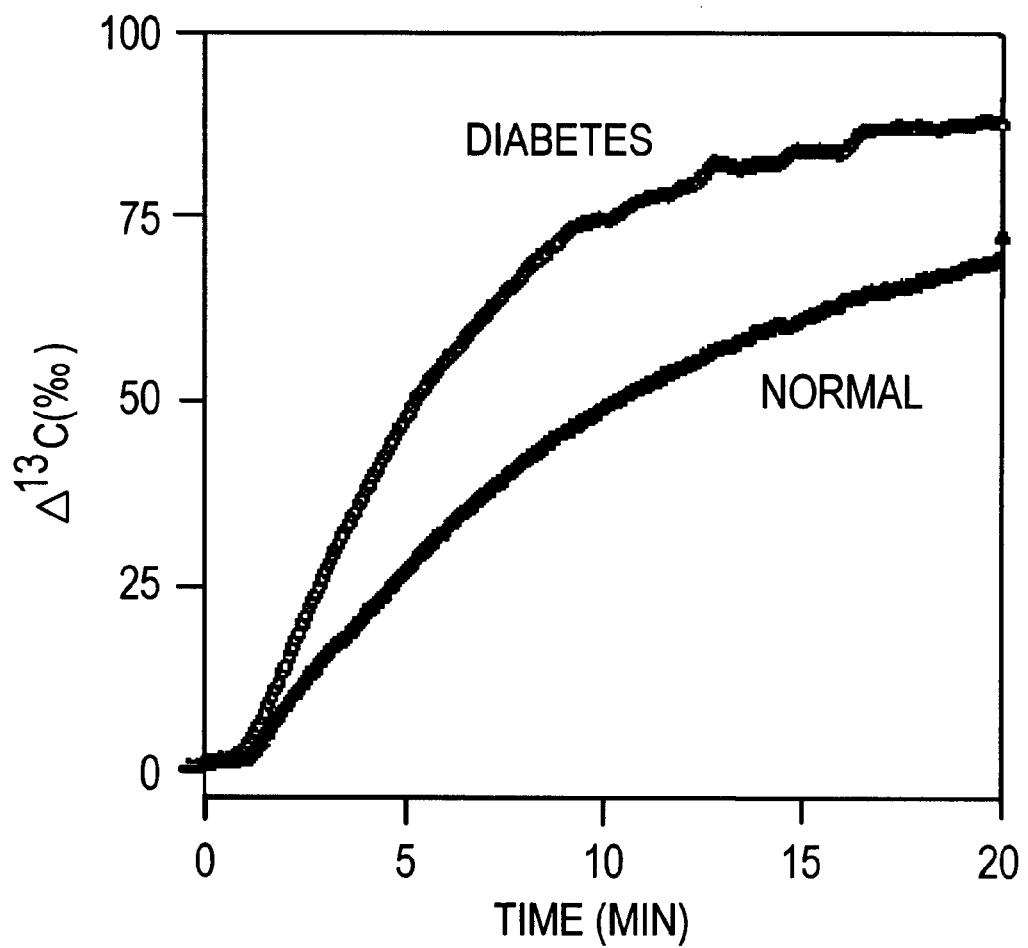
FIG. 4 shows the increase of $^{13}CO_2$ in exhalation after administration of 1-$^{13}C$-fructose.

$\Delta^{13}C$ values (‰) continued increasing up to 20 min after the administration of 1-$^{13}C$-fructose in both the normal and the diabetic rats (FIG. 4).

The $\Delta^{13}C$ value (‰) at 15 min after the administration was 83.51±7.30‰ in the diabetic rats, while the corresponding value was 63.90±7.42‰ in the normal rats. Thus, the value in the diabetic rats was very significantly (p<0.01 (ANOVA with Fischer LSD)) higher than that in the normal rats.

The slope from 2 to 7 min after the administration was 47.87±8.34‰/5 min in the diabetic rats, while the corresponding slope was 29.07±4.08‰/5 min in the normal rats. Thus, the slope in the diabetic rats was significantly (p<0.05 (ANOVA with Fischer LSD)) greater than that in the normal rats.

Accordingly, it is possible to diagnose diabetes from the $\Delta^{13}C$ value (‰) at a specific time after administration of

EXAMPLE 5

2-$^{13}$C-Fructose Breath Test

2-$^{13}$C-fructose (purchased from ICON) dissolved in physiological saline was administered to normal rats (8-week-old; fasting blood sugar level 75±3.1 mg/dl; n=4) and diabetic rats (8-week-old; casual blood sugar level 533.5 mg/dl; fasting blood sugar level 86 mg/dl; n=2) from the femoral vein at a dose of 100 mg/kg. Then, degrees of increase of $^{13}$C levels in exhaled $CO_2$ ($\Delta^{13}C$ (‰)) were measured according to the method described in Example 1.

Figure 5:
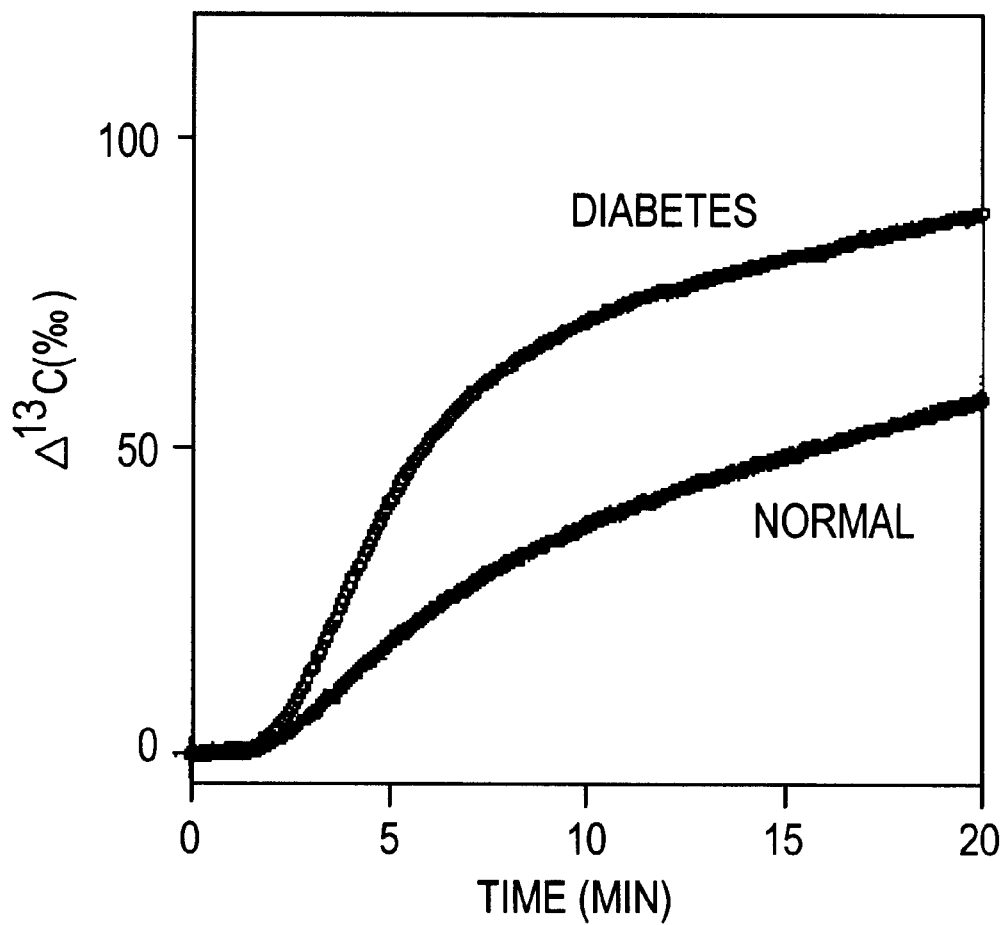
FIG. 5 shows the increase of $^{13}CO_2$ in exhalation after administration of 2-$^{13}C$-fructose.

In the normal rats, $\Delta^3C$ values (‰) continued increasing up to 20 min after the administration of 2-$^{13}$C-fructose. In the diabetic rats, $\Delta^{13}C$ values (‰) increased sharply up to about 8 min after the administration, but thereafter increased gradually up to 20 min (FIG. 5).

The $\Delta^{13}C$ value (‰) at 20 min after the administration was 94.68‰ in the diabetic rats, while the corresponding value was 58.75±2.73‰ in the normal rats. Thus, the value in the diabetic rats was very significantly ($p<0.01$ (ANOVA with Fischer LSD)) higher than that in the normal rats.

The slope from 2 to 6 min after the administration was 47.66‰/4 min in the diabetic rats, while the corresponding slope was 21.4±1.84‰/4 min in the normal rats. Thus, the slope in the diabetic rats was very significantly ($p<0.01$ (ANOVA with Fischer LSD)) greater than that in the normal rats.

Accordingly, it is possible to diagnose diabetes from the $\Delta^{13}C$ value (‰at a specific time after administration of 2-$^{13}$C-fructose or the slope of increase of $\Delta^{13}C$ values (‰) after the administration. With this test, it is possible to diagnose even light diabetes which shows a normal blood sugar level at the time of fasting.

EXAMPLE 6

1-$^{13}$C-Xylose Breath Test

1-$^{13}$C-xylose (purchased from ICON) dissolved in distilled water was administered orally to normal rats (9-week-old; fasting blood sugar level 75.5±2.1 mg/dl; n=4) and diabetic rats (9-week-old; casual blood sugar level 370.3±39.0 mg/dl; fasting blood sugar level 77±9.1 mg/dl; n=4) at a dose of 300 mg/kg. Then, degrees of increase of $^{13}$C levels in exhaled $CO_2$ ($\Delta^{13}C$ (‰)) were measured according to the method described in Example 1.

The $\Delta^{13}C$ value (‰) at 30 min after the administration of 1-$^{13}$C-xylose was 23.40±7.60‰ in the diabetic rats, while the corresponding value was 6.82±3.02‰ in the normal rats. Thus, the value in the diabetic rats was significantly ($p<0.05$ (ANOVA with Fischer LSD)) higher than that in the normal rats.

The slope from 20 to 30 min after the administration was 12.80±2.18‰/10 min in the diabetic rats, while the corresponding slope was 4.61±1.40‰/10 min in the normal rats. Thus, the slope in the diabetic rats was very significantly ($p<0.01$ (ANOVA with Fischer LSD)) greater than that in the normal rats.

Accordingly, it is possible to diagnose diabetes from the $\Delta^{13}C$ value (‰) at a specific time after administration of 1-$^{13}$C-xylose or the slope of increase of $\Delta^{13}C$ values (‰) after the administration. With this test, it is possible to diagnose even light diabetes which shows a normal blood sugar level at the time of fasting.

EXAMPLE 7

U-$^{13}$C-Starch Breath Test

U-$^{13}$C-starch (purchased from Chlorella Industry) dissolved in distilled water was administered orally to normal rats (9-week-old; fasting blood sugar level 57.7±4.5 mg/dl; n-3) and diabetic rats (9-week-old; casual blood sugar level 398.3±24.2 mg/dl; fasting blood sugar level 76.5±7.9 mg/dl; n=4) at a dose of 30 mg/kg. Then, degrees of increase of $^{13}$C levels in exhaled $CO_2$ ($\Delta^{13}C$ (‰)) were measured according to the method described in Example 1.

Figure 6:
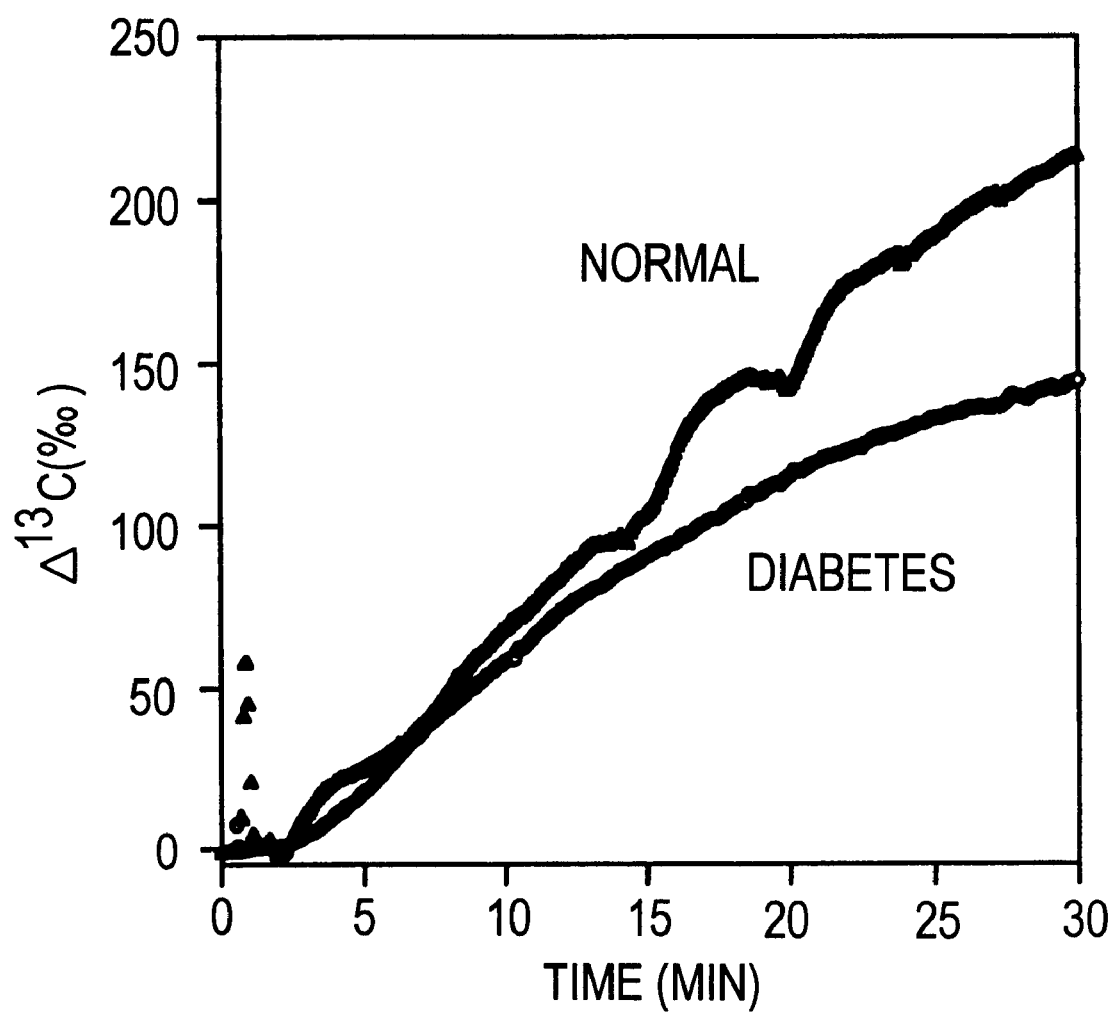
FIG. 6 shows the increase of $^{13}CO_2$ in exhalation after administration of U-$^{13}C$-starch.

A $^{13}$C values (‰) continued increasing up to 20 min after the administration of U-$^{13}$C-starch in both the normal and the diabetic rats (FIG. 6).

The $^{13}$C value (‰) at 30 min after the administration was 144.50±23.27‰ in the diabetic rats, while the corresponding value was 213.89±4.66‰ in the normal rats. Thus, the value in the diabetic rats was very significantly ($p<0.01$ (ANOVA with Fischer LSD)) lower than that in the normal rats.

Accordingly, it is possible to diagnose diabetes from the $\Delta^{13}C$ value (‰) at a specific time after administration of U-$^{13}$C-starch. With this test, it is possible to diagnose even light diabetes which shows a normal blood sugar level at the time of fasting.

EXAMPLE 8

1-$^{13}$C-Isoleucine Breath Test

1-$^{13}$C-isoleucine (purchased from mass Trace) dissolved in physiological saline was administered to normal rats (9-week-old; fasting blood sugar level 80.8±5.5 mg/dl; n=4) and diabetic rats (9-week-old; casual blood sugar level 368.7±55.7 mg/dl; fasting blood sugar level 81.3±6.2 mg/dl; n=3) from the femoral vein at a dose of 20 mg/kg. Then, degrees of increase of $^{13}$C levels in exhaled $CO_2$ ($\Delta^{13}C$ (‰)) were measured according to the method described in Example 1.

Figure 7:
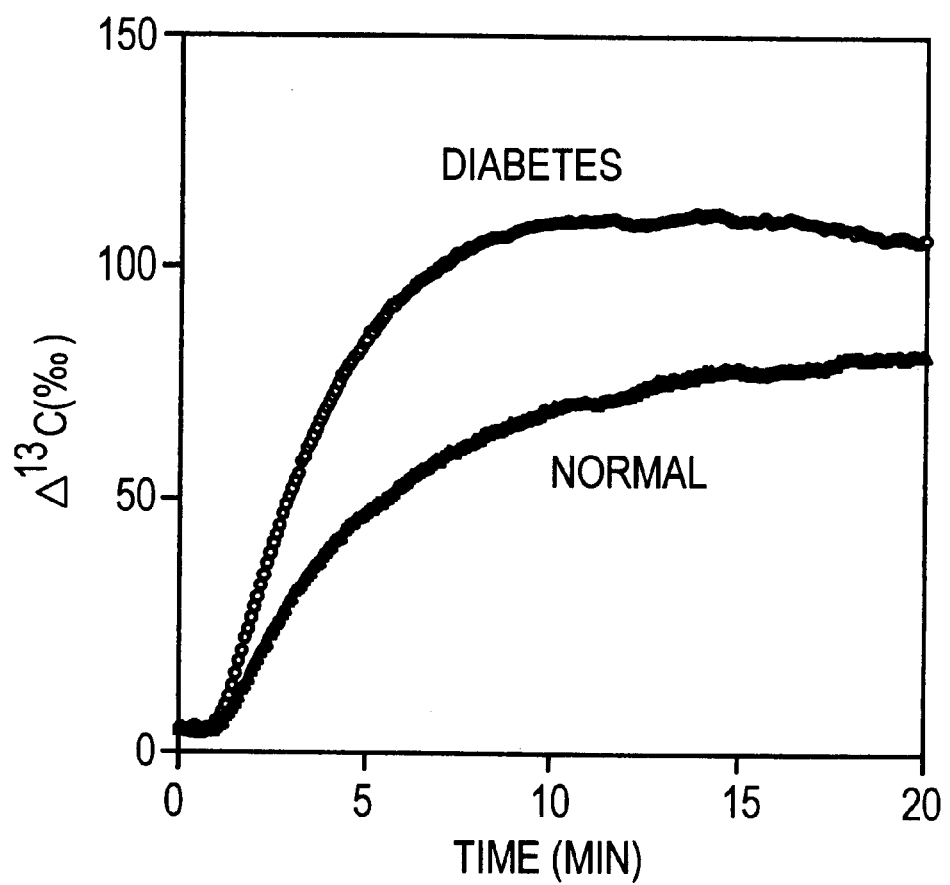
FIG. 7 shows the increase of $^{13}CO_2$ in exhalation after administration of 1-$^{13}C$-isoleucine.

In the normal rats, $\Delta^{13}C$ values (‰) continued increasing up to 20 min after the administration of 1-$^{13}$C-isoleucine. In the diabetic rats, $\Delta^{13}C$ values (‰) increased sharply up to about 9 min after the administration, but thereafter remained at an almost constant level up to 20 min (FIG. 7).

The $\Delta^{13}C$ value (‰) at 5 min after the administration was 83.92±5.53‰ in the diabetic rats, while the corresponding value was 46.98±3.24‰ in the normal rats. Thus, the value in the diabetic rats was very significantly ($p<0.001$ (ANOVA with Fischer LSD)) higher than that in the normal rats.

The slope from 2 to 5 min after the administration was 56.21±2.09‰/3 min in the diabetic rats, while the corresponding slope was 33.21±2.44‰/3 min in the normal rats. Thus, the slope in the diabetic rats was very significantly ($p<0.0001$ (ANOVA with Fischer LSD)) greater than that in the normal rats.

Accordingly, it is possible to diagnose diabetes from the $\Delta^{13}C$ value (‰) at a specific time after administration of 1-$^{13}$C-isoleucine or the slope of increase of $\Delta^{13}C$ values (‰) after the administration. With this test, it is possible to diagnose even light diabetes which shows a normal blood sugar level at the time of fasting.

EXAMPLE 9

1-$^{13}$C-Alanine Breath Test

1-$^{13}$C-alanine (purchased from mass Trace) dissolved in physiological saline was administered to normal rats (8-week-old; fasting blood sugar level 79.5±4.5 mg/dl; n=4) and diabetic rats (8-week-old; casual blood sugar level 445±20.9 mg/dl; fasting blood sugar level 100.8±15.0 mg/dl; n=4) from the femoral vein at a dose of 10 mg/kg. Then, degrees of increase of $^{13}C$ levels in exhaled $CO_2$ ($\Delta^{13}C$ (‰)) were measured according to the method described in Example 1.

Figure 8:
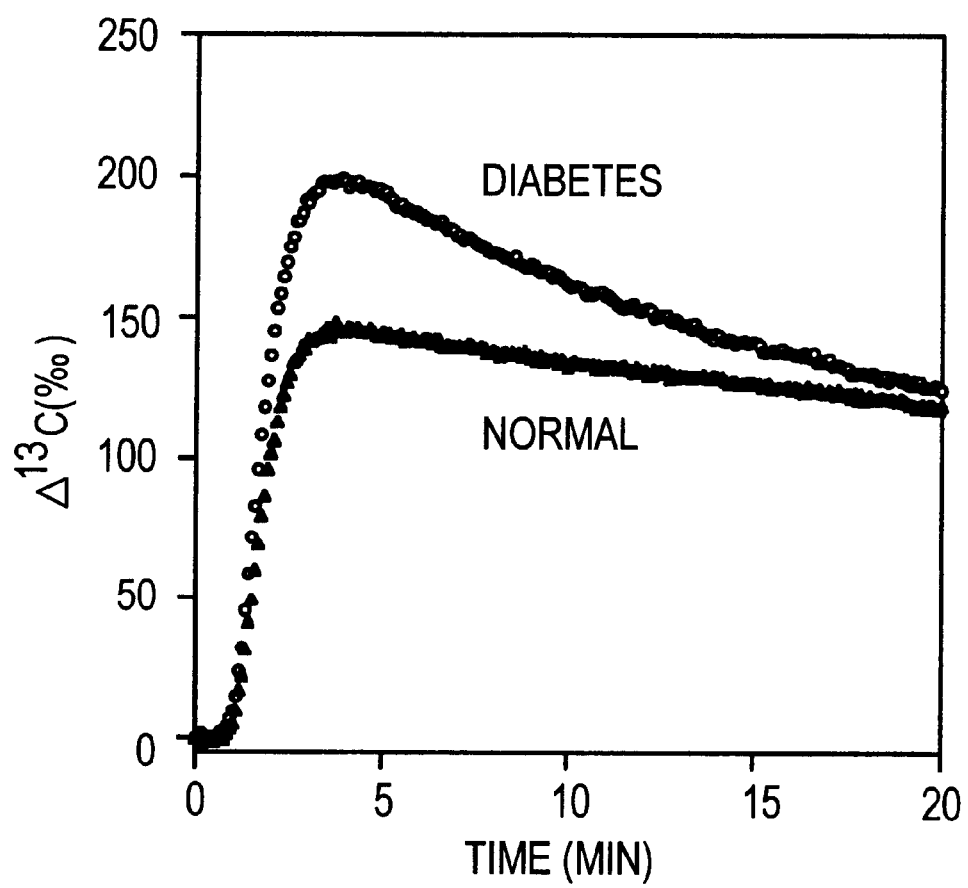
FIG. 8 shows the increase of $^{13}CO_2$ in exhalation after administration of 1-$^{13}C$-alanine.

In both the normal and the diabetic rats, $\Delta^{13}C$ values (‰) sharply increased up to 4 min after the administration of 1-$^{13}C$-alanine, but thereafter decreased gradually up to 20 min (FIG. 8).

The $\Delta^{13}C$ value (‰) at 10 min after the administration was 161.35±6.670 in the diabetic rats, while the corresponding value was 132.16±3.53‰ in the normal rats. Thus, the value in the diabetic rats was very significantly (p<0.01 (ANOVA with Fischer LSD)) higher than that in the normal rats.

The slope from 5 to 15 min after the administration was −52.09±19.38‰/10 min in the diabetic rats, while the corresponding slope was −18.12±7.28‰/10 min in the normal rats. Thus, the slope in the diabetic rats was significantly (p<0.05 (ANOVA with Fischer LSD)) smaller than that in the normal rats.

Accordingly, it is possible to diagnose diabetes from the $\Delta^{13}C$ value (‰) at a specific time after administration of 1-$^{13}C$-alanine or the slope of increase of $\Delta^{13}C$ values (‰) after the administration. With this test, it is possible to diagnose even light diabetes which shows a normal blood sugar level at the time of fasting.

EXAMPLE 10

1-$^{13}C$-Histidine Breath Test

1$^{13}C$-histidine (purchased from ICON) dissolved in physiological saline was administered to normal rats (9-week-old; fasting blood sugar level 73.8±2.3 mg/dl; n=4) and diabetic rats (9-week-old; casual blood sugar level 417.7±36.6 mg/dl; fasting blood sugar level 106.7±5.4 mg/dl; n=3) from the femoral vein at a dose of 30 mg/kg. Then, degrees of increase of $^{13}C$ levels in exhaled $CO_2$ ($\Delta^{13}C$ (‰)) were measured according to the method described in Example 1.

Figure 9:
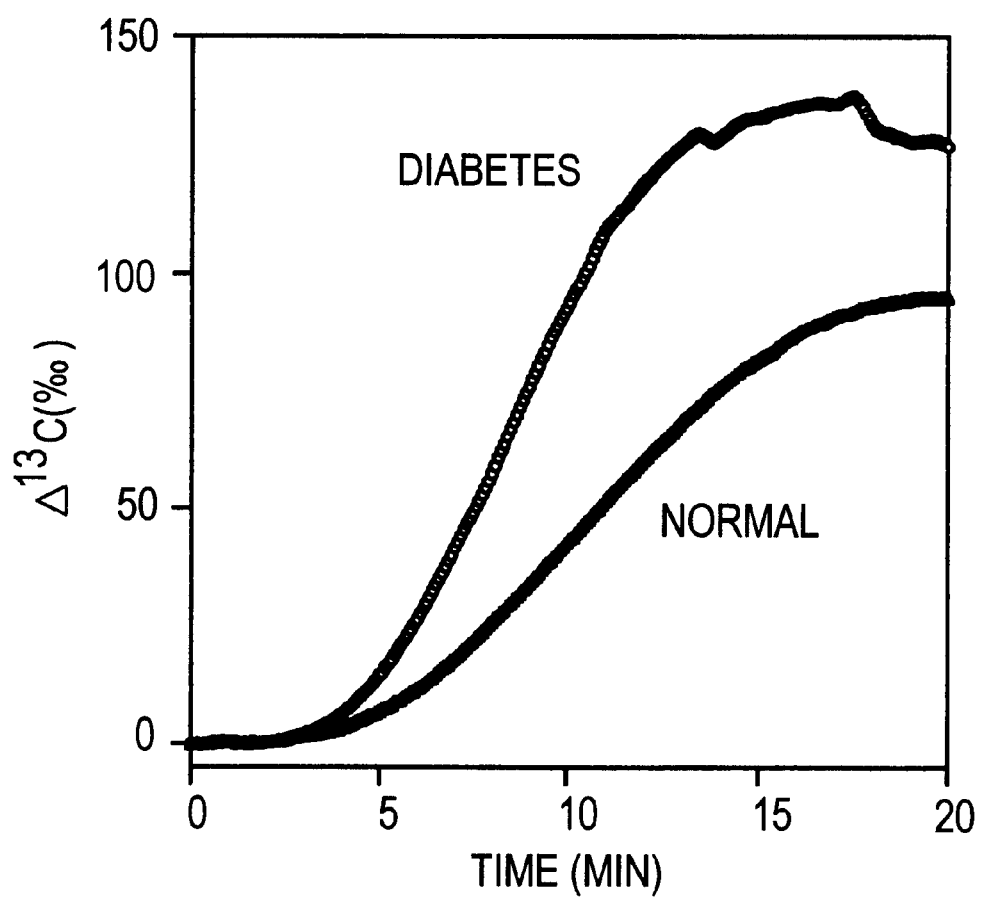
FIG. 9 shows the increase of $^{13}CO_2$ in exhalation after administration of 1-$^{13}C$-histidine.

In the normal rats, $\Delta^{13}C$ values (‰) continued increasing up to 20 min after the administration of 1-$^{13}C$-histidine. In the diabetic rats, $\Delta^{13}C$ values (‰) continued increasing up to about 17 min after the administration, but thereafter decreased gradually up to 20 min (FIG. 9).

The $\Delta^{13}C$ value (‰) at 15 min after the administration was 133.57±2.60‰ in the diabetic rats, while the corresponding value was 81.56±10.84‰ in the normal rats. Thus, the value in the diabetic rats was very significantly (p<0.01 (ANOVA with Fischer LSD)) higher than that in the normal rats.

The slope from 5 to 10 min after the administration was 81.60±2.25‰/5 min in the diabetic rats, while the corresponding slope was 35.91±6.47‰/5 min in the normal rats. Thus, the slope in the diabetic rats was very significantly (p<0.001 (ANOVA with Fischer LSD)) greater than that in the normal rats.

Accordingly, it is possible to diagnose diabetes from the $\Delta^{13}C$ value (‰) at a specific time after administration of 1-$^{13}C$-histidine or the slope of increase of $\Delta^{13}C$ values (‰) after the administration. With this test, it is possible to diagnose even light diabetes which shows a normal blood sugar level at the time of fasting.

EXAMPLE 11

1-$^{13}C$-Valine Breath Test

1-$^{13}C$-valine (purchased from mass Trace) dissolved in physiological saline was administered to normal rats (9-week-old; fasting blood sugar level 76.5±9.9 mg/dl; n=4) and diabetic rats (9-week-old; casual blood sugar level 430±30.5 mg/dl; fasting blood sugar level 99.8±11.1 mg/dl; n=4) from the femoral vein at a dose of 20 mg/kg. Then, degrees of increase of $^{13}C$ levels in exhaled $CO_2$ ($\Delta^{13}C$ (‰)) were measured according to the method described in Example 1.

Figure 10:
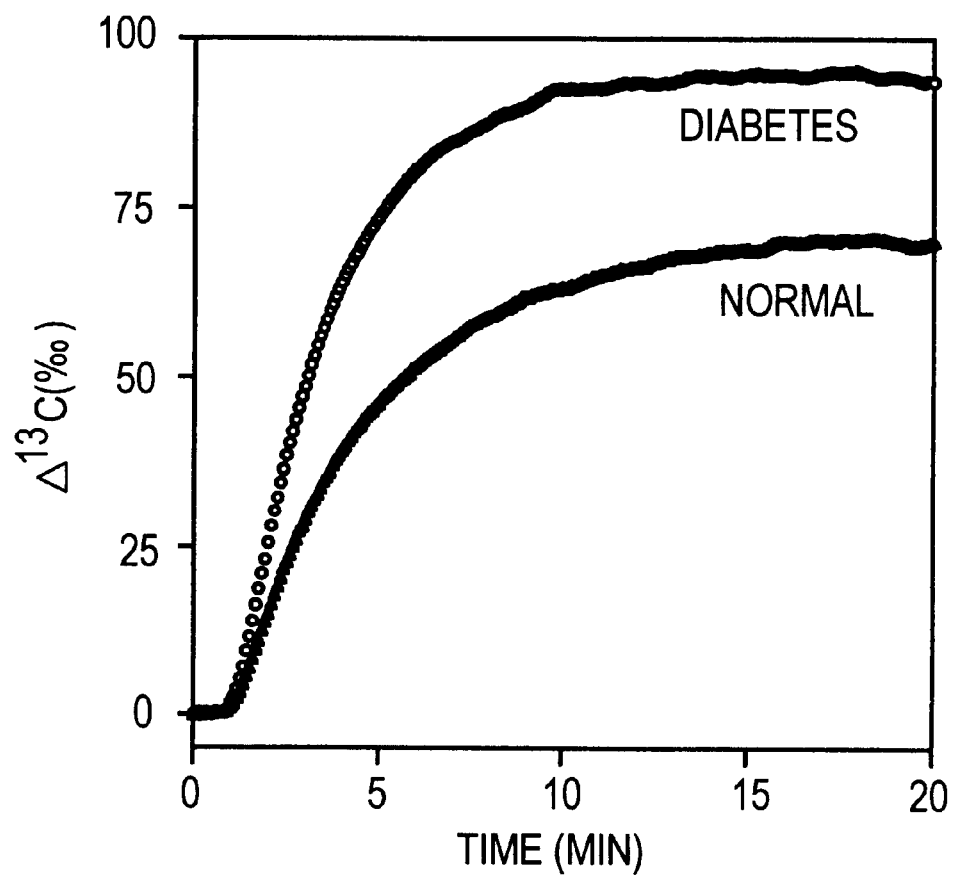
FIG. 10 shows the increase of $^{13}CO_2$ in exhalation after administration of 1-$^{13}C$-valine.

In both the normal and diabetic rats, $\Delta^{13}C$ values (‰) sharply increased up to about 6 min after the administration of 1-$^{13}C$-valine, and thereafter increased gradually up to 20 min (FIG. 10).

The $\Delta^{13}C$ value (‰) at 5 min after the administration was 73.54±7.30‰ in the diabetic rats, while the corresponding value was 45.99±5.62‰ in the normal rats. Thus, the value in the diabetic rats was very significantly (p<0.01 (ANOVA with Fischer LSD)) higher than that in the normal rats.

The slope from 2 to 4 min after the administration was 38.55±3.15‰/2 min in the diabetic rats, while the corresponding slope was 24.17±2.32‰/2 min in the normal rats. Thus, the slope in the diabetic rats was very significantly (p<0.001 (ANOVA with Fischer LSD)) greater than that in the normal rats.

Accordingly, it is possible to diagnose diabetes from the $\Delta^{13}C$ value (‰) at a specific time after administration of 1-$^{13}C$-valine or the slope of increase of $\Delta^{13}C$ values (‰) after the administration. With this test, it is possible to diagnose even light diabetes which shows a normal blood sugar level at the time of fasting.

EXAMPLE 12

1,2-$^{13}C$-Ornithine Hydrochloride Breath Test 1,2-$^{13}C$-ornithine hydrochloride (purchased from ICON) dissolved in physiological saline was administered to normal rats (8-week-old; fasting blood sugar level 67±5.8 mg/dl; n=4) and diabetic rats (8-week-old; casual blood sugar level 411.8±102.5 mg/dl; fasting blood sugar level 77±5.7 mg/dl; n=4) from the femoral vein at a dose of 20 mg/kg. Then, degrees of increase of $^{13}C$ levels in exhaled $CO_2$ ($\Delta^{13}C$ (‰)) were measured according to the method described in Example 1.

Figure 11:
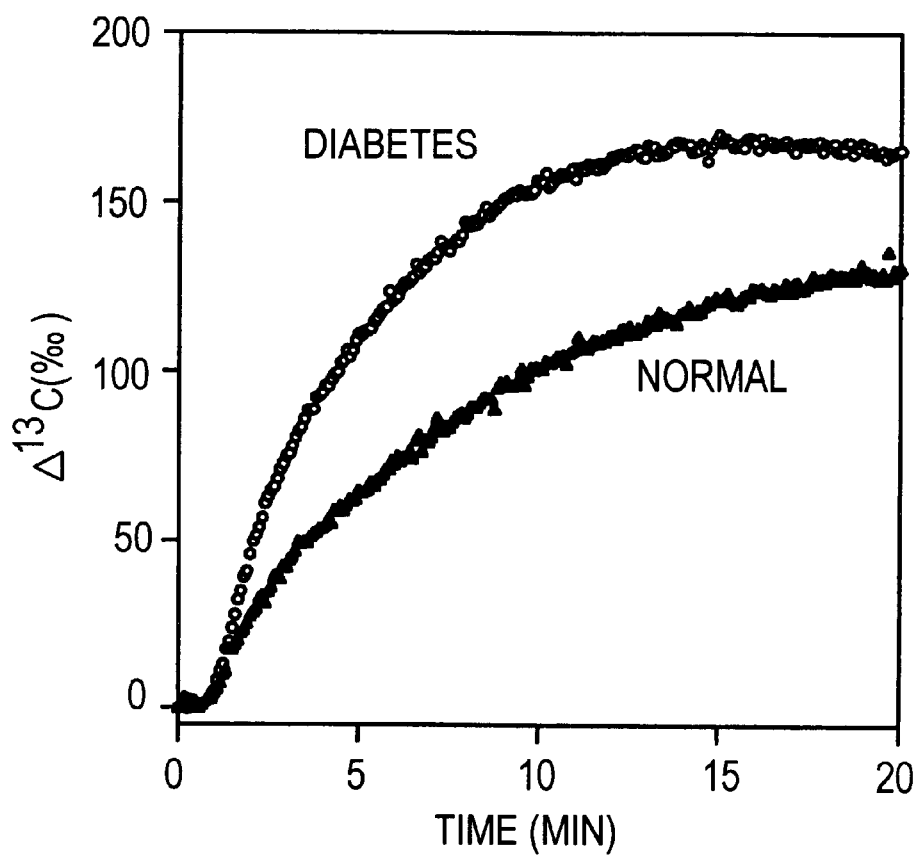
FIG. 11 shows the increase of $^{13}CO_2$ in exhalation after administration of 1,2-$^{13}C$-ornithine hydrochloride.

In the normal rats, $\Delta^{13}C$ values (‰) continued increasing up to 20 min after the administration of 1,2-$^{13}C$-ornithine hydrochloride. In the diabetic rats, $\Delta^{13}C$ values (‰) increased up to about 14 min after the administration, and thereafter remained at an almost constant level up to 20 min (FIG. 11).

The $\Delta^{13}C$ value (‰) at 10 min after the administration was 155.70±17.99‰ in the diabetic rats, while the corresponding value was 100.71±5.97‰ in the normal rats. Thus, the value in the diabetic rats was very significantly (p<0.01 (ANOVA with Fischer LSD)) higher than that in the normal rats.

The slope from 2 to 7 min after the administration was 87.79±12.93‰/5 min in the diabetic rats, while the corresponding slope was 53.56±4.72‰/5 min in the normal rats. Thus, the slope in the diabetic rats was very significantly (p<0.01 (ANOVA with Fischer LSD)) greater than that in the normal rats.

Accordingly, it is possible to diagnose diabetes from the $\Delta^{13}C$ value (‰) at a specific time after administration of 1,2-$^{13}$C-ornithine hydrochloride or the slope of increase of $\Delta^{13}$C values (‰) after the administration. With this test, it is possible to diagnose even light diabetes which shows a normal blood sugar level at the time of fasting.

EXAMPLE 13

1-$^{13}$C-Methionine Breath Test

1-$^{13}$C-methionine (purchased from ICON) dissolved in physiological saline was administered to normal rats (10-week-old; fasting blood sugar level 73.3±2.8 mg/dl; n=4) and diabetic rats (10-week-old; casual blood sugar level 590.5±9.9 mg/dl; fasting blood sugar level 84±5.8 mg/dl; n=4) from the femoral vein at a dose of 40 mg/kg. Then, degrees of increase of $^{13}$C levels in exhaled $CO_2$ ($\Delta^{13}$C (‰)) were measured according to the method described in Example 1.

Figure 12:
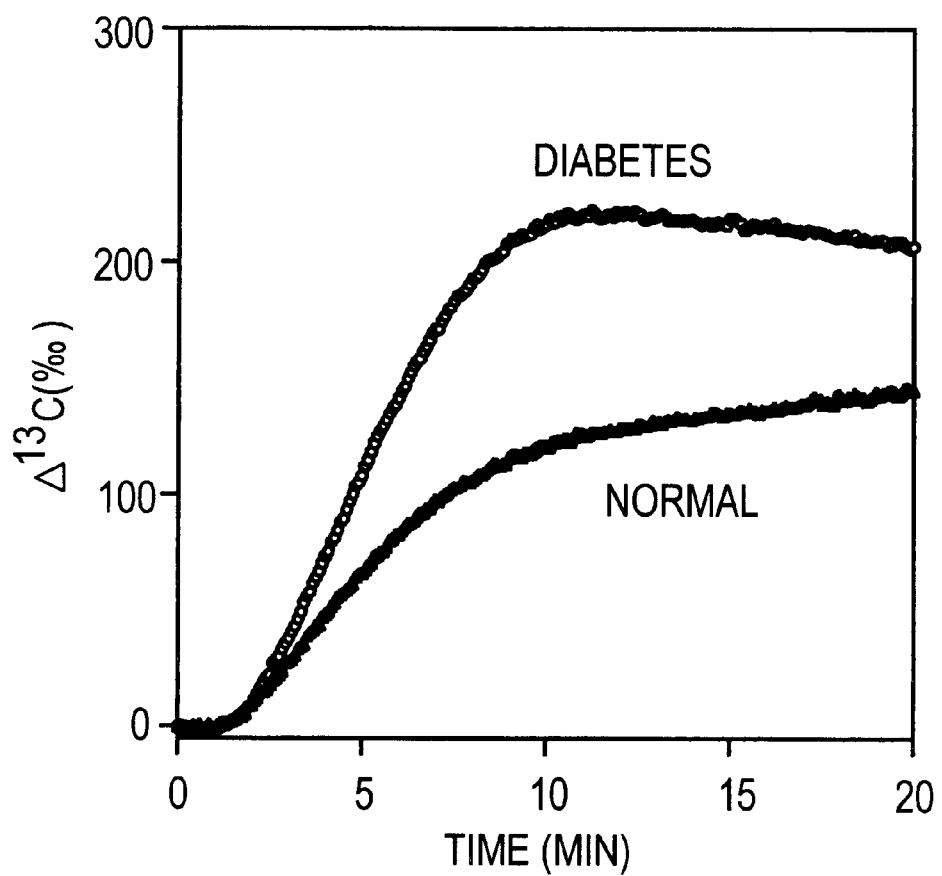
FIG. 12 shows the increase of $^{13}CO_2$ in exhalation after administration of 1-$^{13}C$-methionine.

In the normal rats, $\Delta^{13}$C values (‰) continued increasing up to 20 min after the administration of 1-$^{13}$C-methionine. In the diabetic rats, $\Delta^{13}$C values (‰) increased up to about 10 min after the administration, but thereafter decreased gradually up to 20 min (FIG. 12).

The $\Delta^{13}$C value (‰) at 10 min after the administration was 216.30±30.02‰ in the diabetic rats, while the corresponding value was 120.31±18.84‰ in the normal rats. Thus, the value in the diabetic rats was very significantly (p<0.01 (ANOVA with Fischer LSD)) higher than that in the normal rats.

The slope from 2 to 7 min after the administration was 161.58±24.17‰/5 min in the diabetic rats, while the corresponding slope was 88.17±17.04‰/5 min in the normal rats. Thus, the slope in the diabetic rats was very significantly (p<0.01 (ANOVA with Fischer LSD)) greater than that in the normal rats.

Accordingly, it is possible to diagnose diabetes from the $\Delta^{13}$C value (‰) at a specific time after administration of 1-$^{13}$C-methionine or the slope of increase of L $^{13}$C values (‰) after the administration. with this test, it is possible to diagnose even light diabetes which shows a normal blood sugar level at the time of fasting.

EXAMPLE 14

1-$^{13}$C-Arginine Breath Test

1-$^{13}$C-arginine (purchased from ICON) dissolved in physiological saline was administered to normal rats (8-week-old; fasting blood sugar level 68.8±6.9 mg/dl; n=4) and diabetic rats (8-week-old; casual blood sugar level 419.5±69.3 mg/dl; fasting blood sugar level 83.3±11.8 mg/dl; n=4) from the femoral vein at a dose of 50 mg/kg. Then, degrees of increase of $^{13}$C levels in exhaled $CO_2$ ($\Delta^{13}$C (‰)) were measured according to the method described in Example 1.

Figure 13:
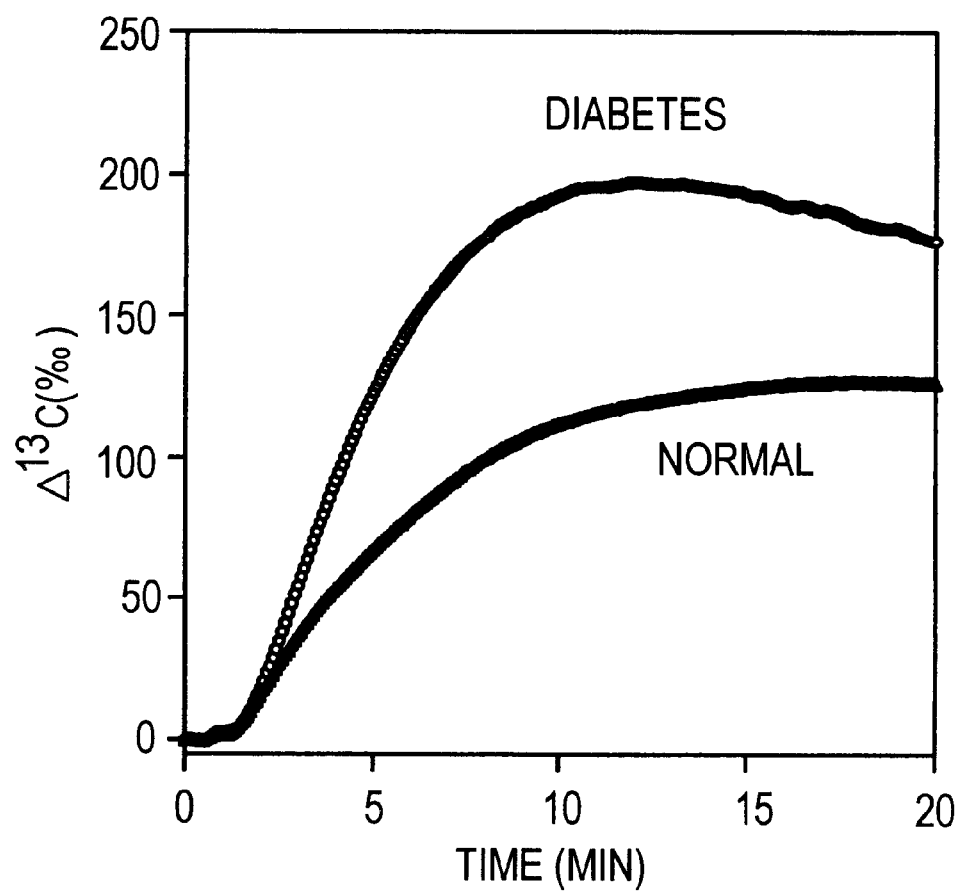
FIG. 13 shows the increase of $^{13}CO_2$ in exhalation after administration of 1-$^{13}C$-arginine.

In the normal rats, $\Delta^{13}$C values (‰) continued increasing up to 20 min after the administration of 1-$^{13}$C-arginine. In the diabetic rats, $\Delta^{13}$C values (‰) increased up to about 12 min after the administration, but thereafter decreased gradually up to 20 min (FIG. 13).

The $\Delta^{13}$C value (‰) at 10 min after the administration was 192.40±30.23‰ in the diabetic rats, while the corresponding value was 111.68±14.15‰ in the normal rats. Thus, the value in the diabetic rats was very significantly (p<0.01 (ANOVA with Fischer LSD)) higher than that in the normal rats.

The slope from 2 to 7 min after the administration was 146.90±18.97‰/5 min in the diabetic rats, while the corresponding slope was 75.02±10.01‰/5 min in the normal rats. Thus, the slope in the diabetic rats was very significantly (p<0.01 (ANOVA with Fischer LSD)) greater than that in the normal rats.

Accordingly, it is possible to diagnose diabetes from the $\Delta^{13}$C value (‰) at a specific time after administration of 1-$^{13}$C-arginine or the slope of increase of $\Delta^{13}$C values (‰) after the administration. With this test, it is possible to diagnose even light diabetes which shows a normal blood sugar level at the time of fasting.

EXAMPLE 15

1-$^{13}$C-Tryptophan Breath Test

1-$^{13}$C-tryptophan (purchased from ICON) dissolved in physiological saline was administered to normal rats (9-week-old; fasting blood sugar level 61±1.6 mg/dl; n=4) and diabetic rats (9-week-old; casual blood sugar level 487±56.5 mg/dl; fasting blood sugar level 94.7±10.4 mg/dl; n=3) from the femoral vein at a dose of 10 mg/kg. Then, degrees of increase of $^{13}$C levels in exhaled $CO_2$ ($\Delta^{13}$C (‰)) were measured according to the method described in Example 1.

Figure 14:
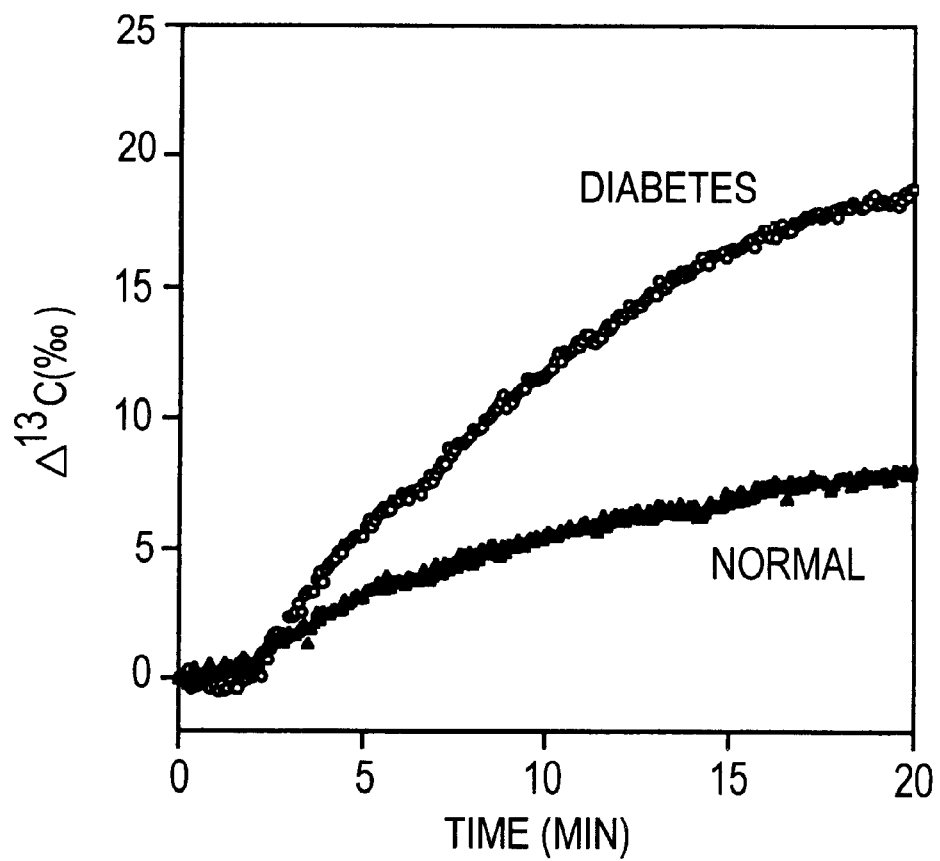
FIG. 14 shows the increase of $^{13}CO_2$ in exhalation after administration of 1-$^{13}C$-tryptophan.

In both the normal and the diabetic rats, $\Delta^{13}$C values (‰) continued increasing up to 20 min after the administration of 1-$^{13}$C-tryptophan (FIG. 14).

The $\Delta^{13}$C value (‰) at 20 min after the administration was 19.42±4.37‰ in the diabetic rats, while the corresponding value was 8.10±0.77‰ in the normal rats. Thus, the value in the diabetic rats was very significantly (p<0.01 (ANOVA with Fischer LSD)) higher than that in the normal rats.

The slope from 10 to 15 min after the administration was 4.46±0.49‰/5 min in the diabetic rats, while the corresponding slope was 1.20±0.93‰/5 min in the normal rats. Thus, the slope in the diabetic rats was very significantly (p<0.01 (ANOVA with Fischer LSD)) greater than that in the normal rats.

Accordingly, it is possible to diagnose diabetes from the $\Delta^{13}$C value (‰) at a specific time after administration of 1-$^{13}$C-tryptophan or the slope of increase of $\Delta^{13}$C values (‰) after the administration. with this test, it is possible to diagnose even light diabetes which shows a normal blood sugar level at the time of fasting.

EXAMPLE 16

1-$^{13}$C-Serine Breath Test

1-$^{13}$C-serine (purchased from ICON) dissolved in physiological saline was administered to normal rats (10-week-old; fasting blood sugar level 69.8±3.8 mg/dl; n=4) and diabetic rats (10-week-old; casual blood sugar level 569±50.3 mg/dl; fasting blood sugar level 93.3±7.6 mg/dl; n=4) from the femoral vein at a dose of 50 mg/kg. Then, degrees of increase of $^{13}$C levels in exhaled $CO_2$ ($\Delta^{13}$C (‰)) were measured according to the method described in Example 1.

Figure 15:
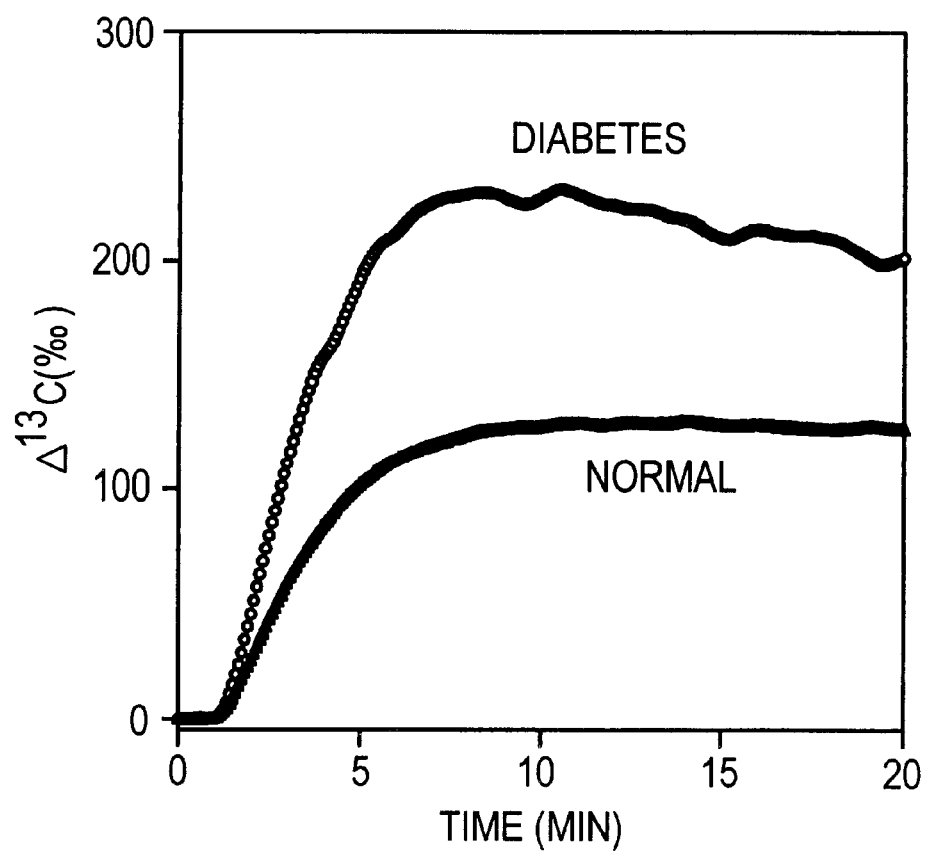
FIG. 15 shows the increase of $^{13}CO_2$ in exhalation after administration of 1-$^{13}C$-serine.

In the normal rats, $\Delta^{13}$C values (‰) increased up to about 8 min after the administration of 1-$^{13}$C-serine, and thereafter remained at an almost constant level. In the diabetic rats, $\Delta^{13}$C values (‰) increased sharply up to about 8 min after the administration, but thereafter decreased gradually up to 20 min (FIG. 15).

The $\Delta^{13}$C value (‰) at 10 min after the administration was 228.08±43.45‰ in the diabetic rats, while the corresponding value was 127.79±10.69‰ in the normal rats. Thus, the value in the diabetic rats was very significantly (p<0.01 (ANOVA with Fischer LSD)) higher than that in the normal rats.

The slope from 1 to 4 min after the administration was 158.13±41.24‰/3 min in the diabetic rats, while the corresponding slope was 84.17±11.38‰/3 min in the normal rats. Thus, the slope in the diabetic rats was significantly (p<0.05 (ANOVA with Fischer LSD)) greater than that in the normal rats.

Accordingly, it is possible to diagnose diabetes from the $\Delta^{13}C$ value (‰) at a specific time after administration of 1-$^{13}C$-serine or the slope of increase of $\Delta^{13}C$ values (‰) after the administration. With this test, it is possible to diagnose even light diabetes which shows a normal blood sugar level at the time of fasting.

EXAMPLE 17

1-$^{13}C$-Tyrosine Breath Test

1-$^{13}C$-tyrosine (purchased from mass Trace) suspended in 0.5% aqueous solution of sodium carboxymethylcellulose was administered orally to normal rats (9-week-old; fasting blood sugar level 79.8±3.9 mg/dl; n=4) and diabetic rats (9-week-old; casual blood sugar level 442±26.8 mg/dl; fasting blood sugar level 86.5±7.4 mg/dl; n=4) at a dose of 60 mg/kg. Then, degrees of increase of $^{13}C$ levels in exhaled $CO_2$ ($\Delta^{13}C$ (‰)) were measured according to the method described in Example 1.

Figure 16:
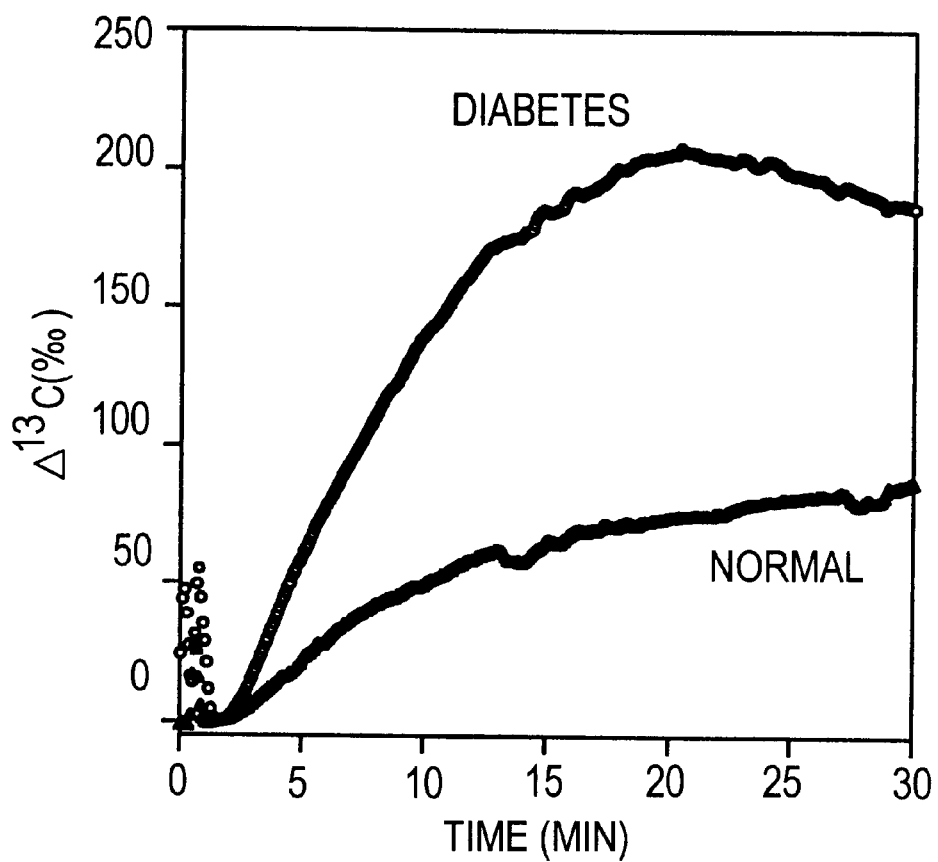
FIG. 16 shows the increase of $^{13}CO_2$ in exhalation after administration of 1-$^{13}C$-tyrosine.

In the normal rats, $\Delta^{13}C$ values (‰) continued increasing up to 30 min after the administration of 1-$^{13}C$-tyrosine. In the diabetic rats, $\Delta^{13}C$ values (‰) increased up to about 20 min after the administration, but thereafter decreased gradually up to 30 min (FIG. 16).

The $\Delta^{13}C$ value (‰) at 20 min after the administration was 205.30±51.43‰ in the diabetic rats, while the corresponding value was 73.96±35.10‰ in the normal rats. Thus, the value in the diabetic rats was significantly (p<0.05 (ANOVA with Fischer LSD)) higher than that in the normal rats.

The slope from 5 to 10 min after the administration was 79.62±19.90‰/5 min in the diabetic rats, while the corresponding slope was 27.52±17.10‰/5 min in the normal rats. Thus, the slope in the diabetic rats was significantly (p<0.05 (ANOVA with Fischer LSD)) greater than that in the normal rats.

Accordingly, it is possible to diagnose diabetes from the $\Delta^{13}C$ value (‰) at a specific time after administration of 1-$^{13}C$-tyrosine or the slope of increase of $\Delta^{13}C$ values (‰) after the administration. With this test, it is possible to diagnose even light diabetes which shows a normal blood sugar level at the time of fasting.

EXAMPLE 18

1-$^{13}C$-Glutamine Breath Test

1$^{13}C$-glutamine (purchased from mass Trace) dissolved in physiological saline was administered to normal rats (8-week-old; fasting blood sugar level 72.8±4.6 mg/dl; n=4) and diabetic rats (8-week-old; casual blood sugar level 491 mg/dl; fasting blood sugar level 88.5 mg/dl; n=2) from the femoral vein at a dose of 20 mg/kg. Then, degrees of increase of $^{13}C$ levels in exhaled $CO_2$ ($\Delta^{13}C$ (‰)) were measured according to the method described in Example 1.

Figure 17:
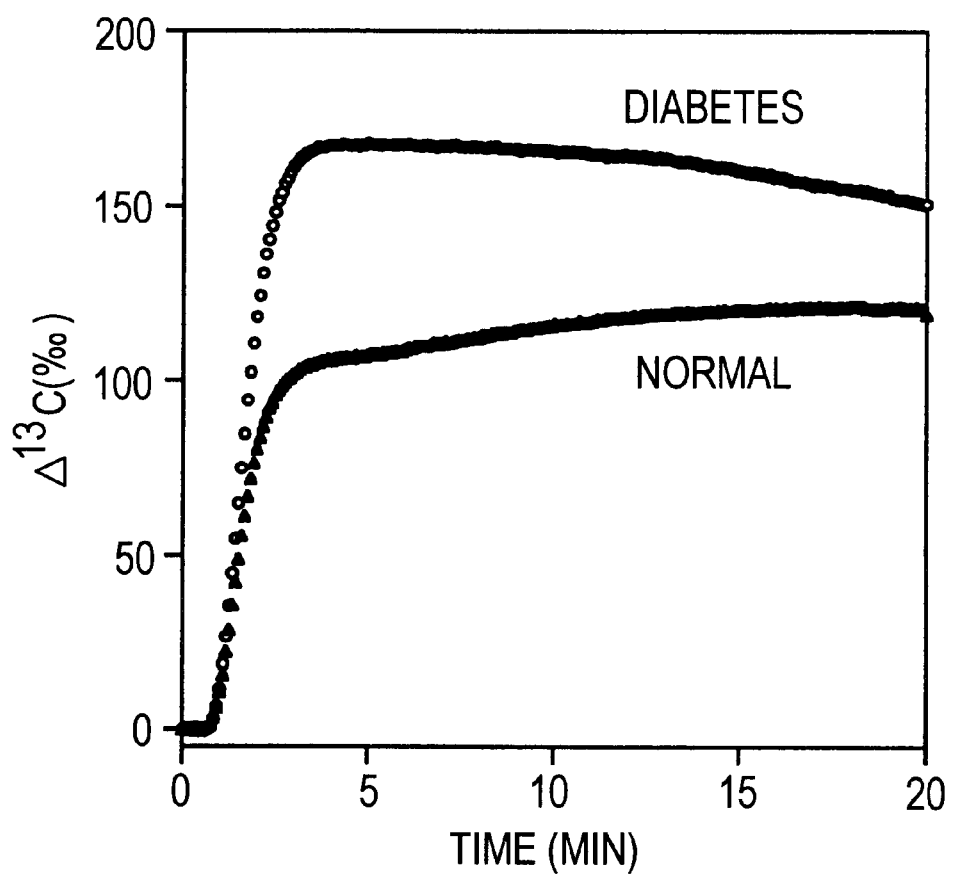
FIG. 17 shows the increase of $^{13}CO_2$ in exhalation after administration of 1-$^{13}C$-glutamine.

In the normal rats, $\Delta^{13}C$ values (‰) increased sharply up to about 3 min after the administration of 1-$^{13}C$-glutamine, and thereafter increased gradually up to 20 min. In the diabetic rats, $\Delta^{13}C$ values (‰) increased sharply up to about 3 min after the administration, but thereafter decreased gradually up to 20 min (FIG. 17).

The $\Delta^{13}C$ value (‰) at 5 min after the administration was 168.18‰ in the diabetic rats, while the corresponding value was 107.17±15.42‰ in the normal rats. Thus, the value in the diabetic rats was significantly (p<0.05 (ANOVA with Fischer LSD)) higher than that in the normal rats.

The slope from 1 to 2 min after the administration was 105.59‰/min in the diabetic rats, while the corresponding slope was 69.88±11.51‰/min in the normal rats. Thus, the slope in the diabetic rats was significantly (p<0.05 (ANOVA with Fischer LSD)) greater than that in the normal rats.

Accordingly, it is possible to diagnose diabetes from the $\Delta^{13}C$ value (‰) at a specific time after administration of 1-$^{13}C$-glutamine or the slope of increase of $^{13}C$ values (‰) after the administration. With this test, it is possible to diagnose even light diabetes which shows a normal blood sugar level at the time of fasting.

EXAMPLE 19

1-l3C-Lysine Hydrochloride Breath Test

1-$^{13}C$-lysine hydrochloride (purchased from mass Trace) dissolved in physiological saline was administered orally to normal rats (8-week-old; fasting blood sugar level 71±1.6 mg/dl; n=3) and diabetic rats (8-week-old; casual blood sugar level 431±71.7 mg/dl; fasting blood sugar level 90.3±4.9 mg/dl; n=3) from the femoral vein at a dose of 50 mg/kg. Then, degrees of increase of $^{13}C$ levels in exhaled $CO_2$ ($\Delta^{13}C$ (‰)) were measured according to the method described in Example 1.

Figure 18:
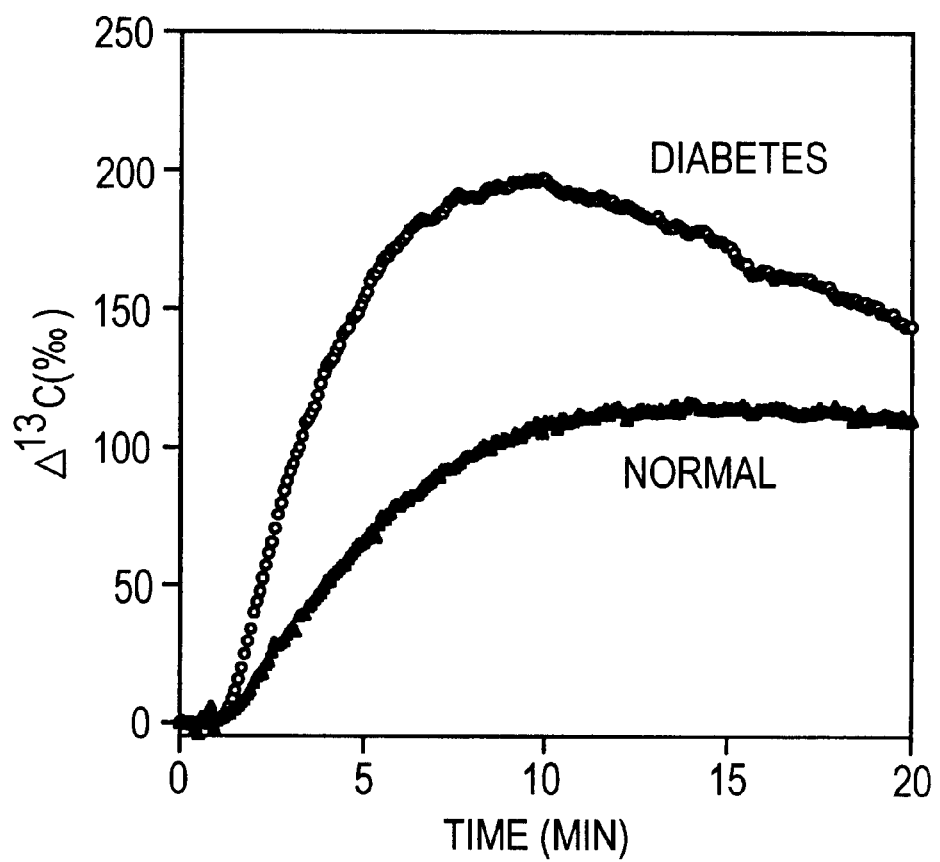
FIG. 18 shows the increase of $^{13}CO_2$ in exhalation after administration of 1-$^{13}C$-lysine hydrochloride.

In the normal rats, $\Delta^{13}C$ values (‰) increased up to about 11 min after the administration of 1-$^{13}C$-lysine hydrochloride, and thereafter remained at an almost constant level up to 20 min. In the diabetic rats, $\Delta^{13}C$ values (‰) increased up to about 10 min after the administration, but thereafter decreased gradually up to 20 min (FIG. 18).

The $\Delta^{13}C$ value (‰) at 8 min after the administration was 181.53±23.82‰ in the diabetic rats, while the corresponding value was 96.95±27.48‰ in the normal rats. Thus, the value in the diabetic rats was significantly (p<0.05 (ANOVA with Fischer LSD)) higher than that in the normal rats.

The slope from 15 to 20 min after the administration was −26.64±5.36‰/5 min in the diabetic rats, while the corresponding slope was −4.58±6.91‰/5 min in the normal rats. Thus, the slope in the diabetic rats was significantly (p<0.05 (ANOVA with Fischer LSD)) smaller than that in the normal rats.

Accordingly, it is possible to diagnose diabetes from the $\Delta^{13}C$ value (‰) at a specific time after administration of 1-$^{13}C$-lysine hydrochloride or the slope of increase of $\Delta^{13}C$ values (‰) after the administration. With this test, it is possible to diagnose even light diabetes which shows a normal blood sugar level at the time of fasting.

EXAMPLE 20

1-$^{13}C$-Glutamic Acid Breath Test

1-$^{13}C$-glutamic acid (purchased from mass Trace) dissolved in physiological saline was administered to normal rats (8-week-old; fasting blood sugar level 70.8±8.3 mg/dl; n=4) and diabetic rats (8-week-old; casual blood sugar level 487.7±38.4 mg/dl; fasting blood sugar level 108±8.8 mg/dl;

n=3) from the femoral vein at a dose of 10 mg/kg. Then, degrees of increase of $^{13}C$ levels in exhaled $CO_2$ ($\Delta^{13}C$ (‰)) were measured according to the method described in Example 1.

Figure 19:
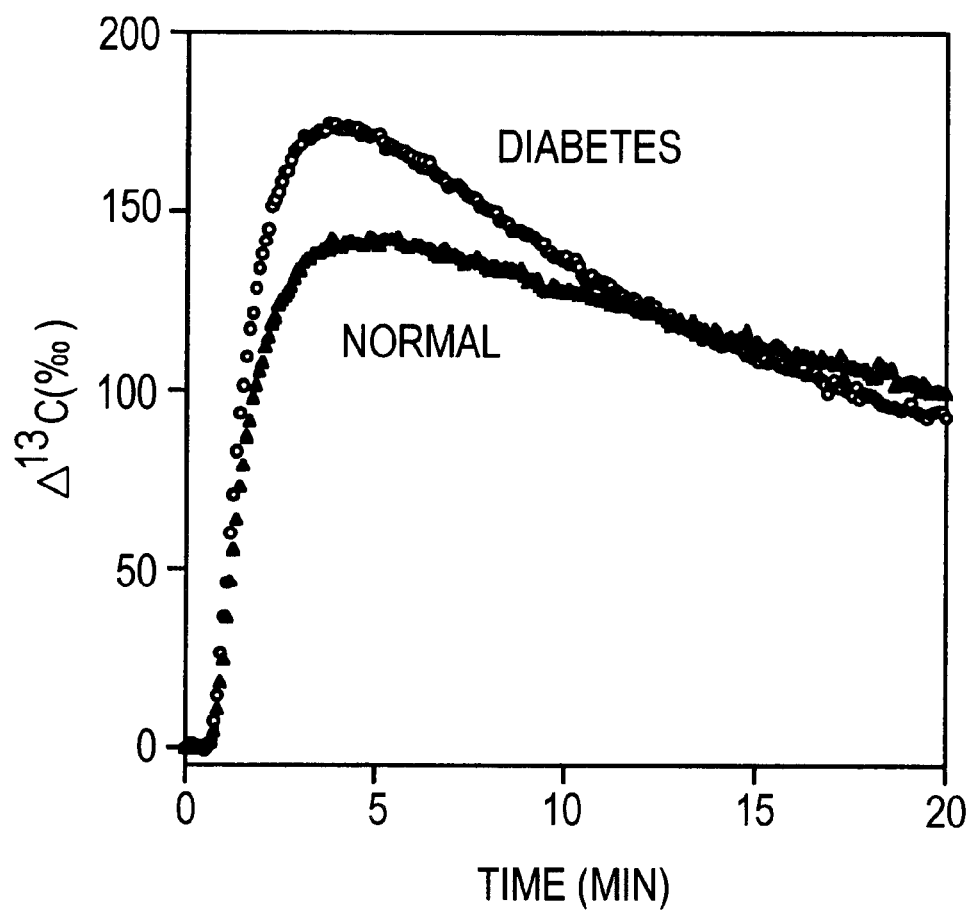
FIG. 19 shows the increase of $^{13}CO_2$ in exhalation after administration of 1-$^{13}C$-glutamic acid.

In both the normal and the diabetic rats, $\Delta^{13}C$ values (‰) increased sharply up to about 4 min after the administration of 1-$^{13}C$-glutamic acid, but thereafter decreased gradually up to 20 min (FIG. 19).

The $\Delta^{13}C$ value (‰) at 4 min after the administration was 170.62±12.18‰ in the diabetic rats, while the corresponding value was 139.95±11.79‰ in the normal rats. Thus, the value in the diabetic rats was significantly (p<(0.05 (ANOVA with Fischer LSD)) higher than that in the normal rats.

The slope from 10 to 20 min after the administration was −43.29±3.47‰/10 min in the diabetic rats, while the corresponding slope was −27.97±5.05‰/10 min in the normal rats. Thus, the slope in the diabetic rats was significantly (p<0.05 (ANOVA with Fischer LSD)) smaller than that in the normal rats.

Accordingly, it is possible to diagnose diabetes from the $\Delta^{13}C$ value (‰) at a specific time after administration of 1-$^{13}C$-glutamic acid or the slope of increase of $\Delta^{13}C$ values (‰) after the administration. With this test, it is possible to diagnose even light diabetes which shows a normal blood sugar level at the time of fasting.

EXAMPLE 21

1-$^{13}C$-Proline Breath Test

1-$^{13}C$-proline (purchased from mass Trace) dissolved in physiological saline was administered to normal rats (10-week-old; fasting blood sugar level 77.6±7.3 mg/dl; n=5) and diabetic rats (10-week-old; casual blood sugar level 430.3±45.2 mg/dl; fasting blood sugar level 97.3±12.5 mg/dl; n=4) from the femoral vein at a dose of 20 mg/kg. Then, degrees of increase of $^{13}C$ levels in exhaled $CO_2$ ($\Delta^{13}C$ (‰)) were measured according to the method described in Example 1.

Figure 20:
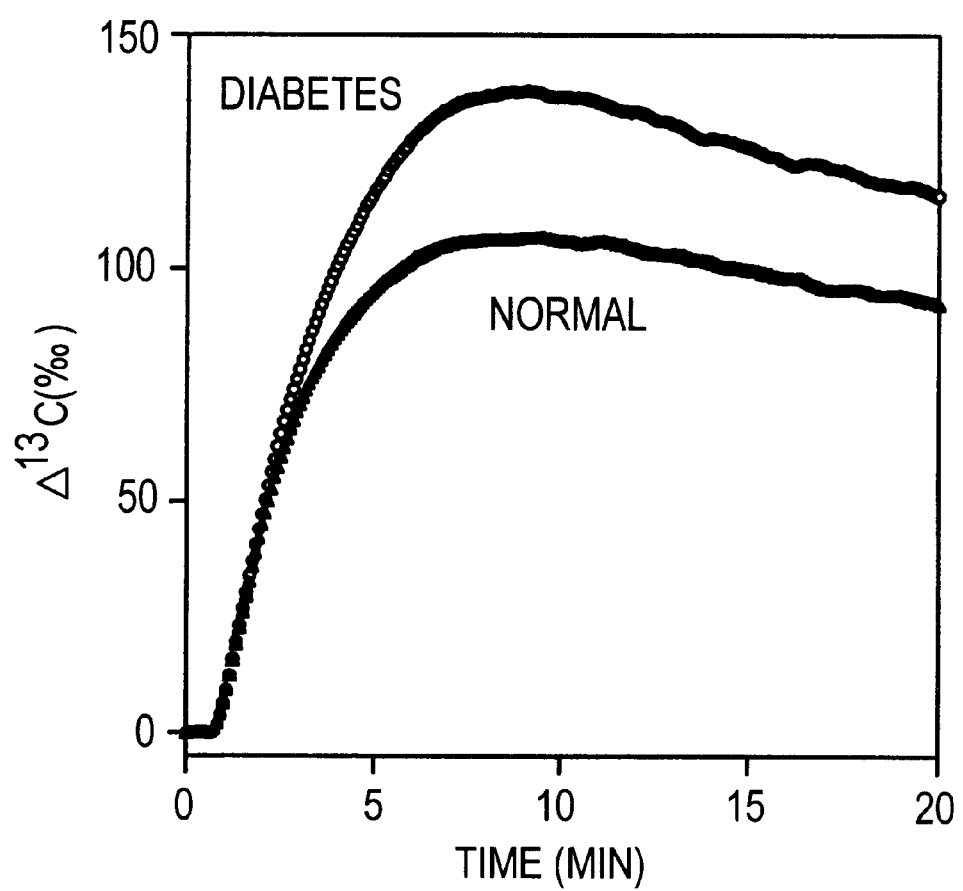
FIG. 20 shows the increase of $^{13}CO_2$ in exhalation after administration of 1-$^{13}C$-proline.

In both the normal and the diabetic rats, $\Delta^{13}C$ values (‰) increased up to about 9 min after the administration of 1-$^{13}C$-proline, but thereafter decreased gradually up to 20 min (FIG. 20).

The $\Delta^{13}C$ value (‰) at 20 min after the administration was 115.77±6.61‰ in the diabetic rats, while the corresponding value was 92.27±11.10‰ in the normal rats. Thus, the value in the diabetic rats was significantly (p<0.05 (ANOVA with Fischer LSD)) higher than that in the normal rats.

Accordingly, it is possible to diagnose diabetes from the $\Delta^{13}C$ value (‰) at a specific time after administration of 1-$^{13}C$-proline. With this test, it is possible to diagnose even light diabetes which shows a normal blood sugar level at the time of fasting.

EXAMPLE 22

1-$^3C$-Glycine Breath Test

1-$^{13}C$-glycine (purchased from mass Trace) dissolved in physiological saline was administered to normal rats (9-week-old; fasting blood sugar level 75.5±5.8 mg/dl; n=4) and diabetic rats (9-week-old; casual blood sugar level 410±10.7 mg/dl; fasting blood sugar level 90±11.9 mg/dl; n=3) from the femoral vein at a dose of 20 mg/kg. Then, degrees of increase of $^{13}C$ levels in exhaled $CO_2$ ($\Delta^{13}C$ (‰)) were measured according to the method described in Example 1.

Figure 21:
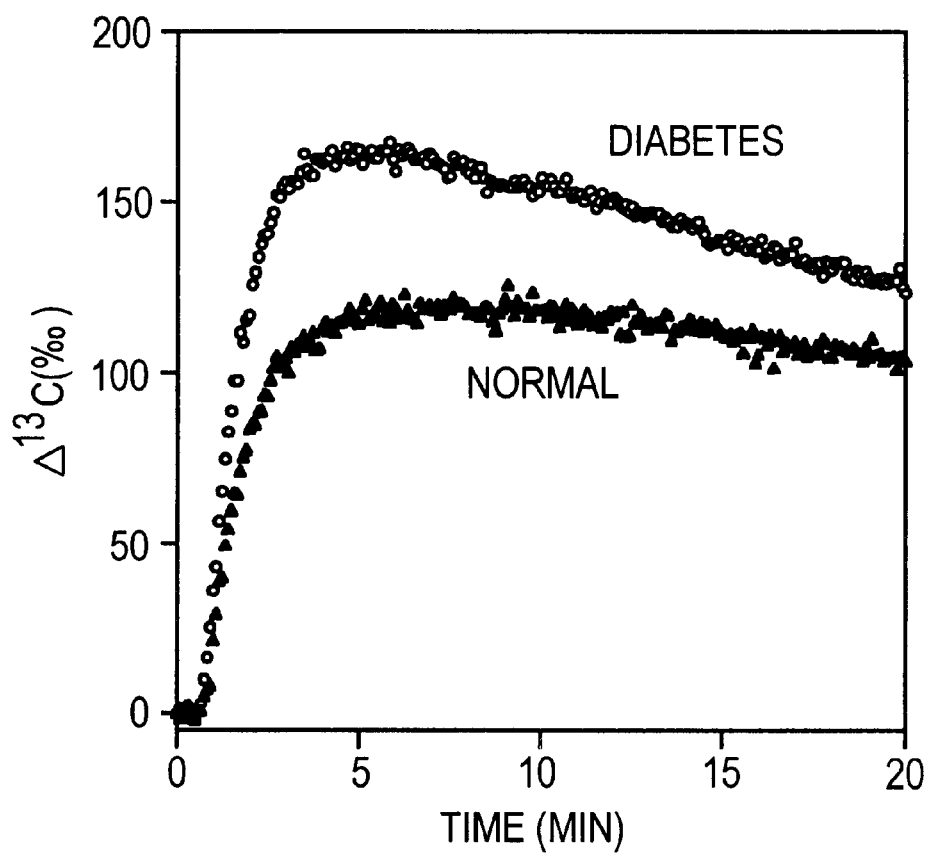
FIG. 21 shows the increase of $^{13}CO_2$ in exhalation after administration of 1-$^{13}C$-glycine.

In the normal rats, $\Delta^{13}C$ values (‰) increased sharply up to about 5 min after the administration of 1-$^{13}C$-glycine, remained at an almost constant level up to about 12 min, but thereafter decreased gradually up to 20 min. In the diabetic rats, $\Delta^{13}C$ values (‰) increased sharply up to about 5 min after the administration, but thereafter decreased gradually up to 20 min (FIG. 21).

The $\Delta^{13}C$ value (‰) at 7 min after the administration was 156.62±10.83‰ in the diabetic rats, while the corresponding value was 119.06±12.19‰ in the normal rats. Thus, the value in the diabetic rats was significantly (p<0.05 (ANOVA with Fischer LSD)) higher than that in the normal rats.

Accordingly, it is possible to diagnose diabetes from the $\Delta^{13}C$ value (‰) at a specific time after administration of 1-$^{13}C$-glycine. With this test, it is possible to diagnose even light diabetes which shows a normal blood sugar level at the time of fasting.

EXAMPLE 23

1-$^{13}C$-Cysteine Breath Test

1-$^{13}C$-cysteine (purchased from ICON) dissolved in physiological saline was administered to normal rats (9-week-old; fasting blood sugar level 74±7.7 mg/dl; n=4) and diabetic rats (9-week-old; casual blood sugar level 457±4.3 mg/dl; fasting blood sugar level 93.7±16.6 mg/dl; n=3) from the femoral vein at a dose of 20 mg/kg. Then, degrees of increase of $^{13}C$ levels in exhaled $CO_2$ ($\Delta^{13}C$ (‰)) were measured according to the method described in Example 1.

The $\Delta^{13}C$ value (‰) at 2 min after the administration of 1-$^{13}C$-cysteine was 42.87±2.09‰ in the diabetic rats, while the corresponding value was 78.97±13.98‰ in the normal rats. Thus, the value in the diabetic rats was significantly (p<0.05 (ANOVA with Fischer LSD)) lower than that in the normal rats.

The slope from 1 to 2 min after the administration was 38.50±2.33‰/min in the diabetic rats, while the corresponding slope was 65.72±10.66‰/min in the normal rats. Thus, the slope in the diabetic rats was significantly (p<0.05 (ANOVA with Fischer LSD)) smaller than that in the normal rats.

Accordingly, it is possible to diagnose diabetes from the $\Delta^{13}C$ value (‰) at a specific time after administration of 1-$^{13}C$-cysteine or the slope of increase of $\Delta^{13}C$ values (‰) after the administration. With this test, it is possible to diagnose even light diabetes which shows a normal blood sugar level at the time of fasting.

EXAMPLE 24

1-$^{13}C$-Leucine Breath Test

1-$^{13}C$-leucine (purchased from mass Trace) dissolved in physiological saline was administered to normal rats (8-week-old; fasting blood sugar level 82.5±4.5 mg/dl; n=4) and diabetic rats (8-week-old; casual blood sugar level 399.5 mg/dl; fasting blood sugar level 85.5 mg/dl; n=2) from the femoral vein at a dose of 10 mg/kg. Then, degrees of increase of $\Delta^{13}C$ levels in exhaled $CO_2$ ($\Delta^{13}C$ (‰)) were measured according to the method described in Example 1.

The $\Delta^{13}C$ value (‰) at 5 min after the administration of 1-$^{13}C$-leucine was 52.89±10.83‰ in the diabetic rats, while the corresponding value was 42.56±2.43‰ in the normal rats. Thus, the value in the diabetic rats was very significantly (p<0.01 (ANOVA with Fischer LSD)) lower than that in the normal rats.

Accordingly, it is possible to diagnose diabetes from the $\Delta^{13}C$ value (‰) at a specific time after administration of 1-$^{13}$C-leucine. With this test, it is possible to diagnose even light diabetes which shows a normal blood sugar level at the time of fasting.

EXAMPLE 25

1-$^{13}$C-Aspartic Acid Breath Test

1-$^{13}$C-aspartic acid (purchased from mass Trace) dissolved in physiological saline was administered to normal rats (8-week-old; fasting blood sugar level 56.3±6.8 mg/dl; n=4) and diabetic rats (8-week-old; casual blood sugar level 389±52.1 mg/dl;.fasting blood sugar level 80.5±6.1 mg/dl; n=4) from the femoral vein at a dose of 10 mg/kg. Then, degrees of increase of $^{13}C$ levels in exhaled $CO_2$ ($\Delta^{13}C$ (‰)) were measured according to the method described in Example 1.

Figure 22:
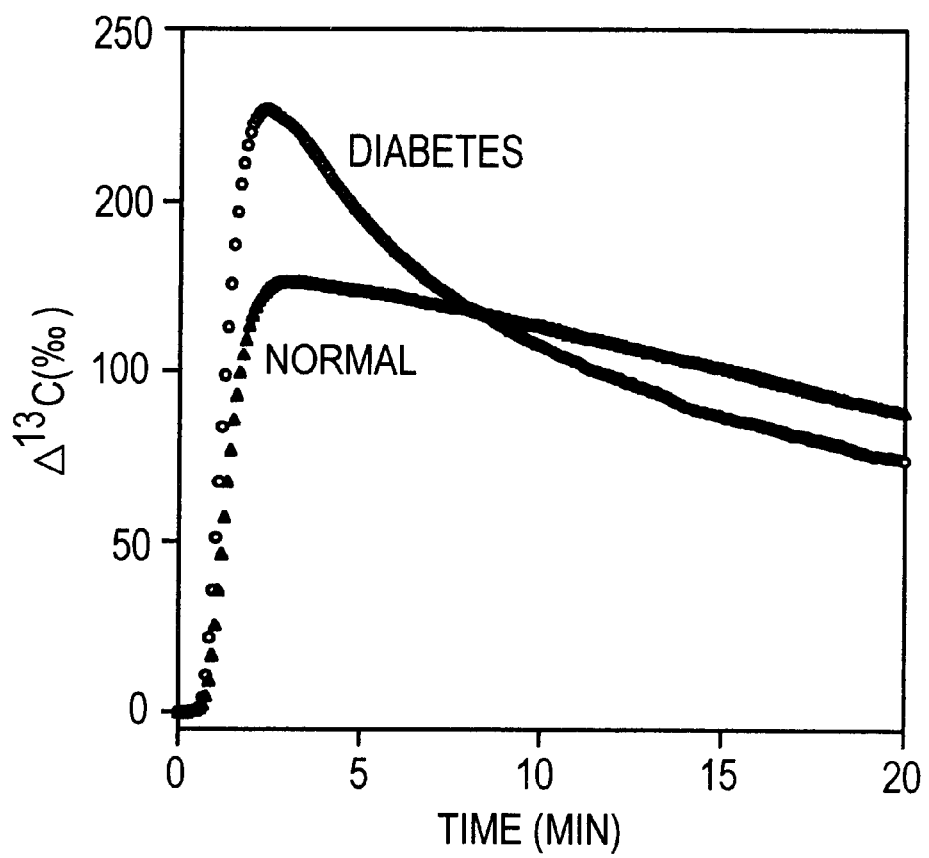
FIG. 22 shows the increase of $^{13}CO_2$ in exhalation after administration of 1-$^{13}$C-aspartic acid.

In both the normal and the diabetic rats, $\Delta^{13}C$ values (‰) increased sharply up to about 2 min after the administration of 1-$^{13}$C-aspartic acid, but thereafter decreased gradually up to 20 min (FIG. 22).

The $\Delta^{13}C$ value (‰) at 3 min after the administration was 172.66±8.65‰ in the diabetic rats, while the corresponding value was 126.56±13.45‰ in the normal rats. Thus, the value in the diabetic rats was very significantly (p<0.01 (ANOVA with Fischer LSD)) higher than that in the normal rats.

The slope from 3 to 8 min after the administration was −53.79±11.42‰/5 min in the diabetic rats, while the corresponding slope was −8.13±10.84‰/5 min in the normal rats. Thus, the slope in the diabetic rats was very significantly (p<0.01 (ANOVA with Fischer LSD)) smaller than that in the normal rats.

Accordingly, it is possible to diagnose diabetes from the $\Delta^{13}C$ value (‰) at a specific time after administration of 1-$^{13}$C-aspartic acid or the slope of increase of $\Delta^{13}C$ values (‰) after the administration. With this test, it is possible to diagnose even light diabetes which shows a normal blood sugar level at the time of fasting.

EXAMPLE 26

1,1-$^{13}$C-Cystine Breath Test

1-$^{13}$C-cystine (purchased from mass Trace) suspended in 0.5% aqueous solution of sodium carboxymethylcellulose was administered orally to normal rats (9-week-old; fasting blood sugar level 65.5±6.4 mg/dl; n=4) and diabetic rats (9-week-old; casual blood sugar level 324.5±7.7 mg/dl; fasting blood sugar level 81.8±11.5 mg/dl; n=4) at a dose of 45 mg/kg. Then, degrees of increase of $^{13}C$ levels in exhaled $CO_2$ ($\Delta^{13}C$ (‰)) were measured according to the method described in Example 1.

Figure 23:
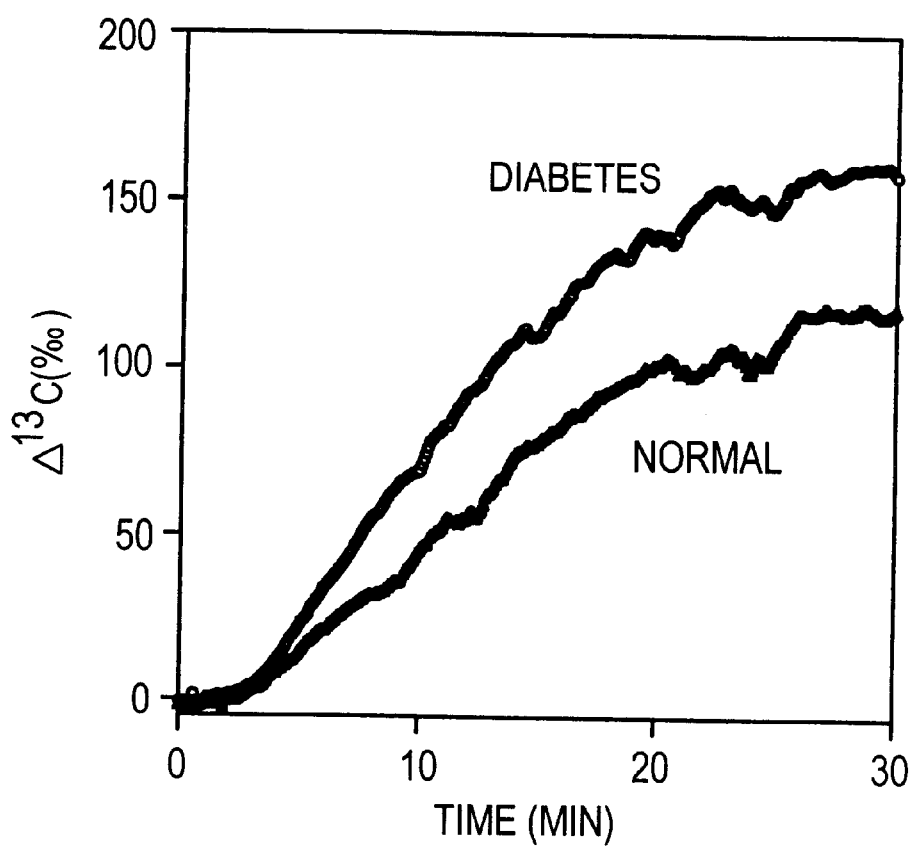
FIG. 23 shows the increase of $^{13}CO_2$ in exhalation after administration of 1,1-$^{13}$C-cystine.

In both the normal and the diabetic rats, $\Delta^{13}C$ values (‰) continued increasing up to 30 min after the administration of 1-$^{13}$C-cystine (FIG. 23).

The $\Delta^{13}C$ value (‰) at 10 min after the administration was 69.15±6.44‰ in the diabetic rats, while the corresponding value was 45.26±8.68‰ in the normal rats. Thus, the value in the diabetic rats was very significantly (p<0.01 (ANOVA with Fischer LSD)) higher than that in the normal rats.

The slope from 5 to 10 min after the administration was 46.82±2.94‰/5 min in the diabetic rats, while the corresponding slope was 30.86±10.06‰/5 min in the normal rats. Thus, the slope in the diabetic rats was significantly (p<0.05 (ANOVA with Fischer LSD)) greater than that in the normal rats.

Accordingly, it is possible to diagnose diabetes from the $\Delta^{13}C$ value (‰) at a specific time after administration of 1-$^{13}$C-cystine or the slope of increase of $\Delta^{13}C$ values (‰) after the administration. With this test, it is possible to diagnose even light diabetes which shows a normal blood sugar level at the time of fasting.

EXAMPLE 27

3-$^{13}$C-Lactic Acid Breath Test

3-$^{13}$C-sodium lactate (purchased from mass Trace) dissolved in physiological saline was administered to normal rats (8-week-old; fasting blood sugar level 67.8±6.5 mg/dl; n=4) and diabetic rats (8-week-old; casual blood sugar level 412.8±71.7 mg/dl; fasting blood sugar level 88.5±17.2 mg/dl; n=4) from the femoral vein at a dose of 50 mg/kg. Then, degrees of increase of $^{13}C$ levels in exhaled $CO_2$ ($\Delta^{13}C$ (‰)) were measured according to the method described in Example 1.

Figure 24:
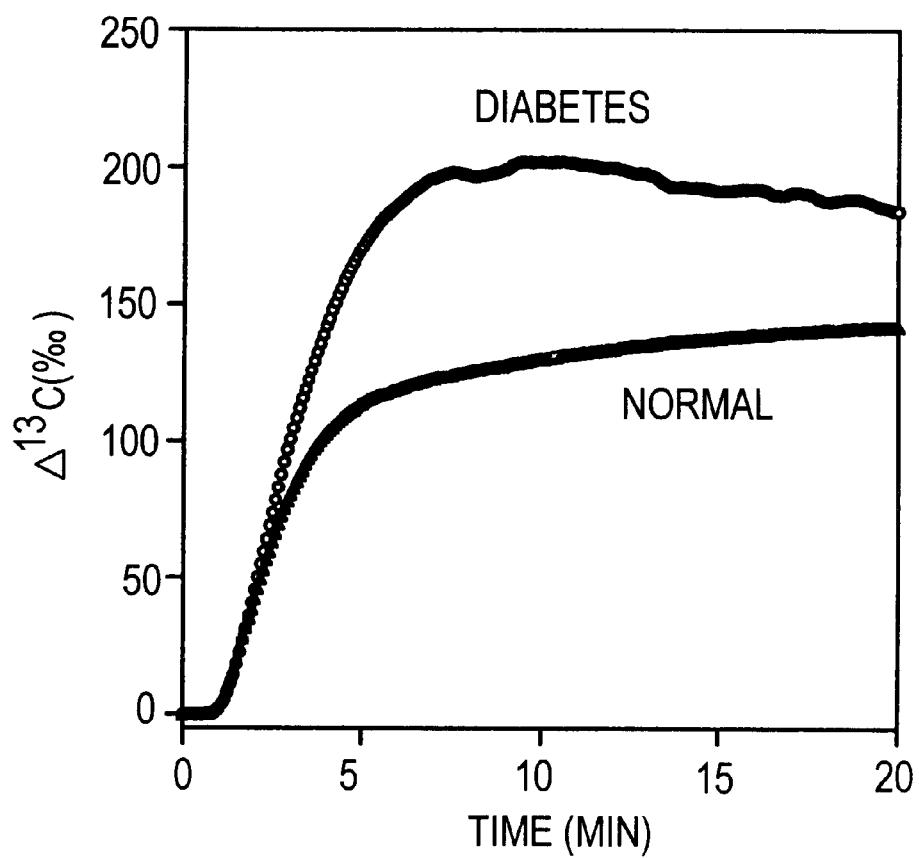
FIG. 24 shows the increase of $^{13}CO_2$ in exhalation after administration of 3-$^{13}$C-lactic acid.

In the normal rats, $\Delta^{13}C$ values (‰) increased sharply up to about 5 min after the administration of 3-$^{13}$C-sodium lactate, and thereafter increased gradually up to 20 min. In the diabetic rats, A $^{13}C$ values (‰) increased sharply up to about 7 min after the administration, but thereafter decreased gradually up to 20 min (FIG. 24).

The $^{13}C$ value (‰) at 10 min after the administration was 202.08±6.05‰ in the diabetic rats, while the corresponding value was 130.30±11.47‰ in the normal rats. Thus, the value in the diabetic rats was very significantly (p<0.0001 (ANOVA with Fischer LSD)) higher than that in the normal rats.

The slope from 2 to 4 min after the administration was 96.83±17.69‰/2 min in the diabetic rats, while the corresponding slope was 60.69±6.80‰/2 min in the normal rats. Thus, the slope in the diabetic rats was significantly (p<0.05 (ANOVA with Fischer LSD)) greater than that in the normal rats.

Accordingly, it is possible to diagnose diabetes from the $\Delta^{13}C$ value (‰) at a specific time after administration of 3-$^{13}$C-sodium lactate or the slope of increase of $\Delta^{13}C$ values (‰) after the administration. With this test, it is possible to diagnose even light diabetes which shows a normal blood sugar level at the time of fasting.

EXAMPLE 28

1,6-$^{13}$C-Citric Acid Breath Test 1,6-$^{13}$C-citric acid (purchased from ICON) dissolved in physiological saline was administered to normal rats (8-week-old; fasting blood sugar level 66.3±9.6 mg/dl; n=4) and diabetic rats (8-week-old; casual blood sugar level 376.5±57.3 mg/dl; fasting blood sugar level 76.5±16.6 mg/dl; n=4) from the femoral vein at a dose of 5 mg/kg. Then, degrees of increase of $^{1.3}C$ levels in exhaled $CO_2$ ($\Delta^{13}C$ (‰)) were measured according to the method described in Example 1.

The $\Delta^{13}C$ value (‰) at 20 min after the administration of 1,6-$^{13}$C-citric acid was 54.38±3.34‰ in the diabetic rats, while the corresponding value was 67.49±1.82‰ in the normal rats. Thus, the value in the diabetic rats was very significantly (p<0.01 (ANOVA with Fischer LSD)) lower than that in the normal rats.

The slope from 10 to 14 min after the administration was −10.45±1.30‰/4 min in the diabetic rats, while the corresponding slope was −5.81±0.92‰/4 min in the normal rats. Thus, the slope in the diabetic rats was very significantly (p<0.01 (ANOVA with Fischer LSD)) smaller than that in the normal rats.

Accordingly, it is possible to diagnose diabetes from the $\Delta^{13}C$ value (‰) at a specific time after administration of 1,6-$^{13}C$-citric acid or the slope of increase of $\Delta^{13}C$ values (‰) after the administration. With this test, it is possible to diagnose even light diabetes which shows a normal blood sugar level at the time of fasting.

EXAMPLE 29

1-$^{13}C$-Acetic Acid Breath Test

1-$^{13}C$-acetic acid (purchased from mass Trace) dissolved in physiological saline was administered to normal rats (8-week-old; fasting blood sugar level 73.8±5.1 mg/dl; n=4) and diabetic rats 8-week-old; casual blood sugar level 398.3±57.5 mg/dl; fasting blood sugar level 75.0±8.3 mg/dl; n=3) from the femoral vein at a dose of 10 mg/kg. Then, degrees of increase of $^{13}C$ levels in exhaled $CO_2$ ($\Delta^{13}C$ (‰)) were measured according to the method described in Example 1.

Figure 25:
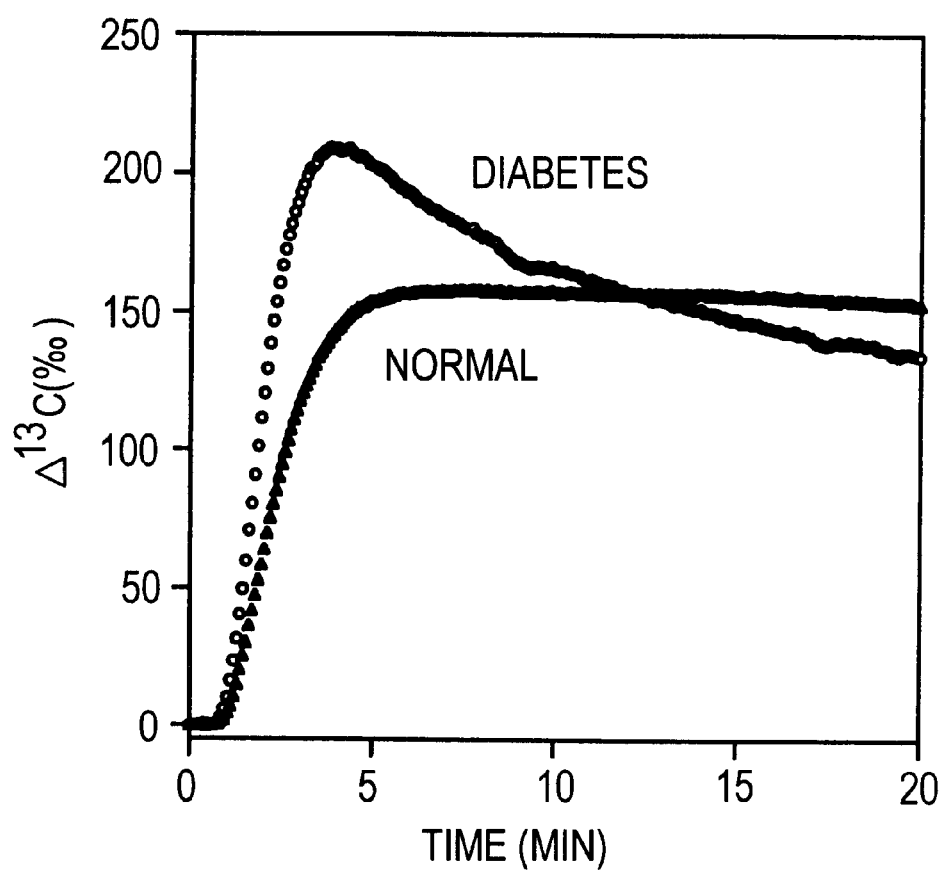
FIG. 25 shows the increase of $^{13}CO_2$ in exhalation after administration of 1-$^{13}$C-acetic acid.

In the normal rats, $\Delta^{13}C$ values (‰) increased sharply up to about 5 min after the administration of 1-$^{13}C$-acetic acid, and thereafter remained at an almost constant level up to 20 min. In the diabetic rats, $\Delta^{13}C$ values (‰) increased sharply up to about 4 min after the administration, but thereafter decreased gradually up to 20 min (FIG. 25).

The $\Delta^{13}C$ value (‰) at 3 min after the administration was 193.09±25.69‰ in the diabetic rats, while the corresponding value was 117.50±8.74V in the normal rats. Thus, the value in the diabetic rats was very significantly (p<0.01 (ANOVA with Fischer LSD)) higher than that in the normal rats.

The slope from 10 to 20 min after the administration was −31.25±13.00‰/10 min in the diabetic rats, while the corresponding slope was −4.67±8.49‰/10 min in the normal rats. Thus, the slope in the diabetic rats was significantly (p<0.05 (ANOVA with Fischer LSD)) smaller than that in the normal rats.

Accordingly, it is possible to diagnose diabetes from the $\Delta^{13}C$ value (‰) at a specific time after administration of 1-$^{13}C$-acetic acid or the slope of increase of $\Delta^{13}C$ values (‰) after the administration. With this test, it is possible to diagnose even light diabetes which shows a normal blood sugar level at the time of fasting.

EXAMPLE 30

1-$^3C$-Oleic Acid Breath Test

1-$^{13}C$-oleic acid (purchased from ICON) emulsified with Tween 20 (0.1%) and physiological saline was administered to normal rats (9-week-old; fasting blood sugar level 74.8±9.8 mg/dl; n=4) and diabetic rats (9-week-old; casual blood sugar level 402.5±31.9 mg/dl; fasting blood sugar level 83.5±4.4 mg/dl; n=4) from the femoral vein at a dose of 70 mg/kg. Then, degrees of increase of $^{13}C$ levels in exhaled $CO_2$ ($\Delta^{13}C$ (‰)) were measured according to the method described in Example 1.

Figure 26:
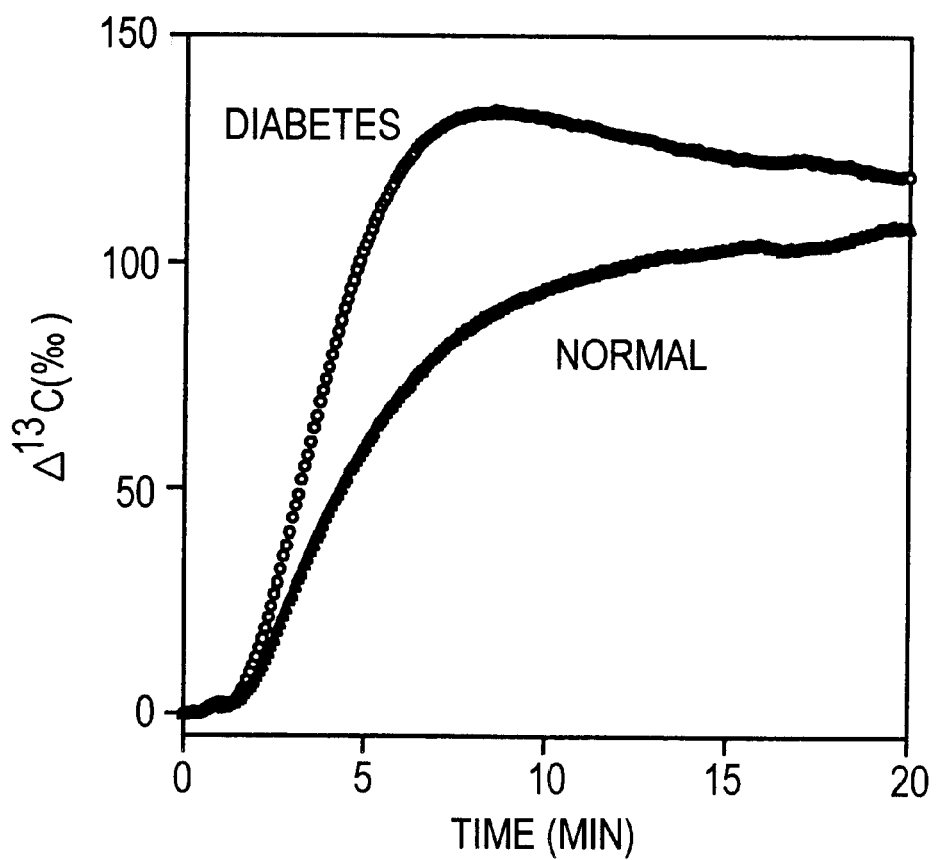
FIG. 26 shows the increase of $^{13}CO_2$ in exhalation after administration of 1-$^{13}$C-oleic acid.

In the normal rats, $\Delta^{13}C$ values (‰) continued increasing up to 20 min after the administration of 1-$^{13}C$-oleic acid. In the diabetic rats, $\Delta^{13}C$ values (‰) increased sharply up to about 8 min after the administration, but thereafter decreased gradually up to 20 min (FIG. 26).

The $\Delta^{13}C$ value (‰) at 8 min after the administration was 132.93±7.09‰ in the diabetic rats, while the corresponding value was 86.51±14.72‰ in the normal rats. Thus, the value in the diabetic rats was very significantly (p<0.01 (ANOVA with Fischer LSD)) higher than that in the normal rats.

The slope from 10 to 20 min after the administration was −12.79±3.72‰/10 min in the diabetic rats, while the corresponding slope was 13.61±4.58‰/10 min in the normal rats. Thus, the slope in the diabetic rats was significantly (p<0.001 (ANOVA with Fischer LSD)) smaller than that in the normal rats.

Accordingly, it is possible to diagnose diabetes from the $\Delta^{13}C$ value (‰) at a specific time after administration of 1-$^{13}C$-oleic acid or the slope of increase of $\Delta^{13}C$ values (‰) after the administration. With this test, it is possible to diagnose even light diabetes which shows a normal blood sugar level at the time of fasting.

EXAMPLE 31

1-$^{13}C$-Palmitic Acid Breath Test

1-$^{13}C$-palmitic acid (purchased from mass Trace) emulsified with Tween 20 (0.2%) and physiological saline was administered to normal rats (9-week-old; fasting blood sugar level 74.8±7.1 mg/dl; n=4) and diabetic rats (9-week-old; casual blood sugar level 422.8±42.0 mg/dl; fasting blood sugar level 80.8±5.1 mg/dl; n=4) from the femoral vein at a dose of 50 mg/kg. Then, degrees of increase of $^{13}C$ levels in exhaled $CO_2$ ($\Delta^{13}C$ (‰)) were measured according to the method described in Example 1.

Figure 27:
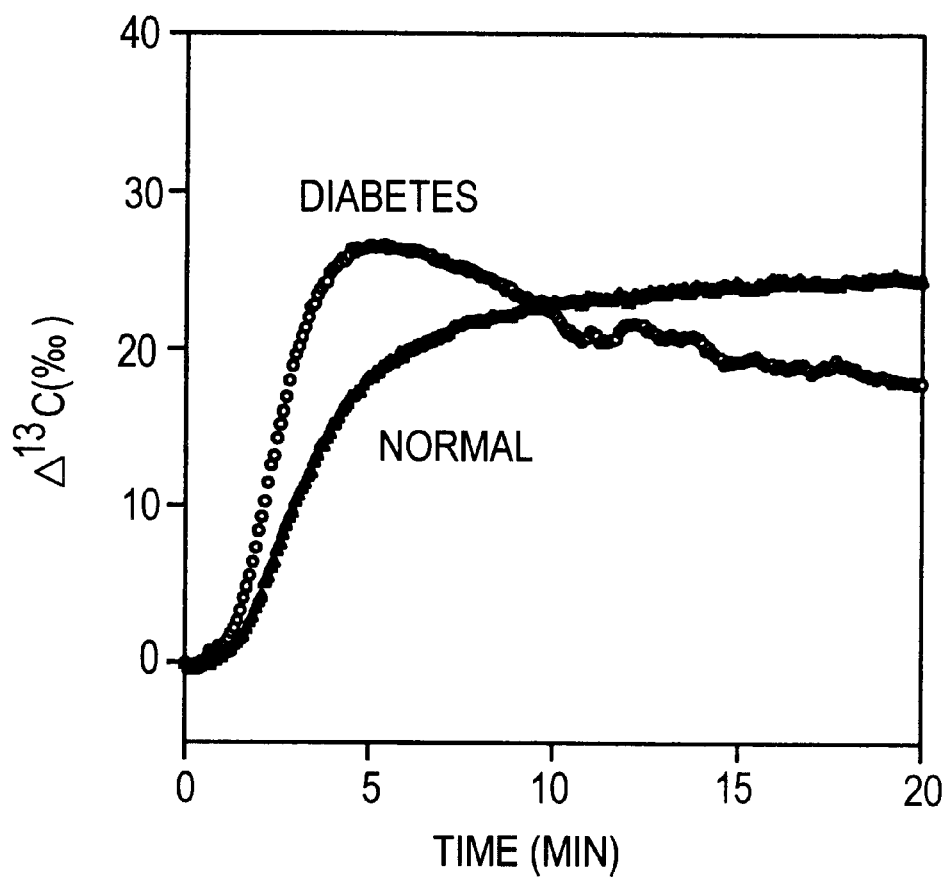
FIG. 27 shows the increase of $^{13}CO_2$ in exhalation after administration of 1-$^{13}$C-palmitic acid.

In the normal rats, $\Delta^{13}C$ values (‰) continued increasing up to 20 min after the administration of 1-$^{13}C$-palmitic acid. In the diabetic rats, $\Delta^{13}C$ values (‰) increased sharply up to about 5 min after the administration, but thereafter decreased gradually up to 20 min (FIG. 27).

The slope from 10 to 20 min after the administration was −4.40±2.21‰/10 min in the diabetic rats, while the corresponding slope was 1.43±1.33‰/10 min in the normal rats. Thus, the slope in the diabetic rats was very significantly (p<0.01 (ANOVA with Fischer LSD)) smaller than that in the normal rats.

Accordingly, it is possible to diagnose diabetes from the slope of increase of $\Delta^{13}C$ values (‰) after the administration of 1-$^{13}C$-palmitic acid. With this test, it is possible to diagnose even light diabetes which shows a normal blood sugar level at the time of fasting.

EXAMPLE 32

1-$^{13}C$-Octanoic Acid Breath Test

1-$^{13}C$-octanoic acid (purchased from mass Trace) emulsified with Tween 20 (0.2%) and physiological saline was administered to normal rats (9-week-old; fasting blood sugar level 78.3±4.7 mg/dl; n=4) and diabetic rats (9-week-old; casual blood sugar level 440.3±38.1 mg/dl; fasting blood sugar level 89.8±9.4 mg/dl; n=4) from the femoral vein at a dose of 30 mg/kg. Then, degrees of increase of $^{13}C$ levels in exhaled $CO_2$ ($\Delta^{13}C$ (‰)) were measured according to the method described in Example 1.

Figure 28:
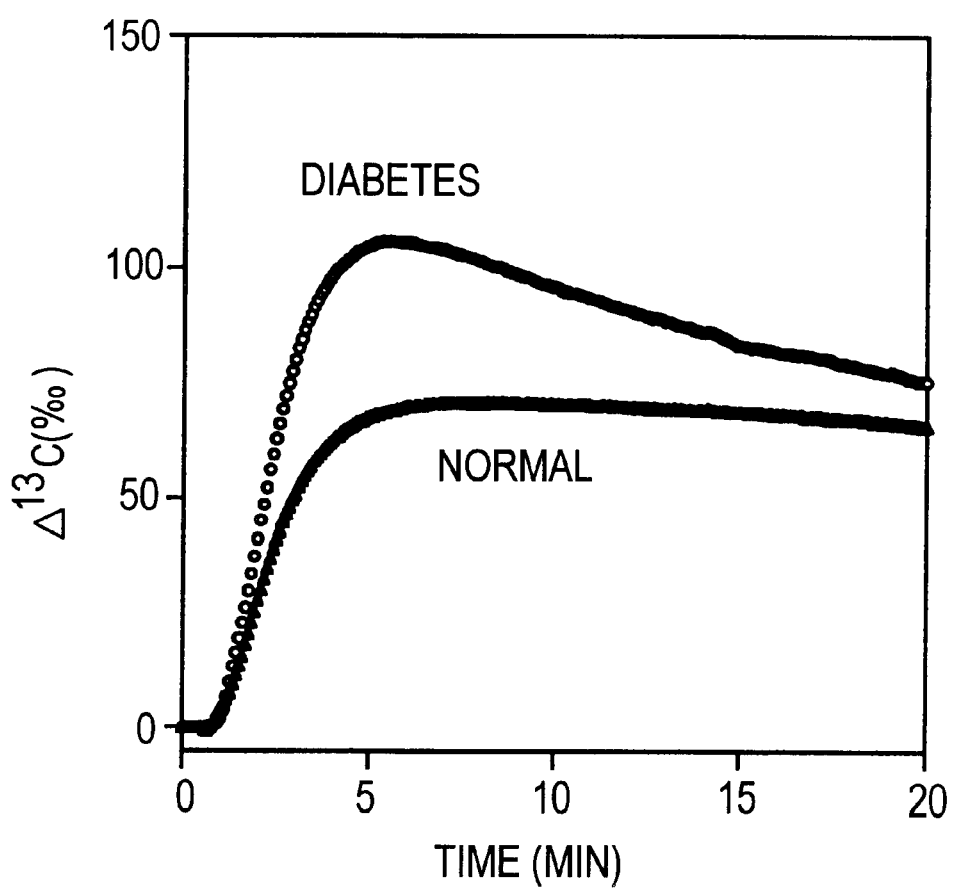
FIG. 28 shows the increase of $^{13}CO_2$ in exhalation after administration of 1-$^{13}$C-octanoic acid.

In the normal rats, $\Delta^{13}C$ values (‰) increased sharply up to about 5 min after the administration of 1-$^{13}C$-octanoic acid, and thereafter remained at an almost constant level up to 20 min. In the diabetic rats, $\Delta^{13}C$ values (‰) increased sharply up to about 5 min after the administration, but thereafter decreased gradually up to 20 min (FIG. 28).

The slope from 10 to 20 min after the administration was −20.55±7.75‰/10 min in the diabetic rats, while the corresponding slope was −4.76±4.41‰/10 min in the normal rats. Thus, the slope in the diabetic rats was significantly (p<0.05 (ANOVA with Fischer LSD)) smaller than that in the normal rats.

Accordingly, it is possible to diagnose diabetes from the slope of increase of $\Delta^{13}C$ values (‰) after the administration of $1\text{-}^{13}C$-octanoic acid. With this test, it is possible to diagnose even light diabetes which shows a normal blood sugar level at the time of fasting.

EXAMPLE 33

$1,1,1\text{-}^{13}C$-Trioctanoin Breath Test $1,1,1\text{-}^{13}C$-trioctanoin (purchased from mass Trace) dissolved in olive oil was administered orally to normal rats (8-week-old; fasting blood sugar level 75.5±8.4 mg/dl; n=4) and diabetic rats (8-week-old; casual blood sugar level 406.8±61.4 mg/dl; fasting blood sugar level 76.8±6.1 mg/dl; n=4) at a dose of 50 mg/kg. Then, degrees of increase of $^{13}C$ levels in exhaled $CO_2$ ($\Delta^{13}C$ (‰)) were measured according to the method described in Example 1.

Figure 29:
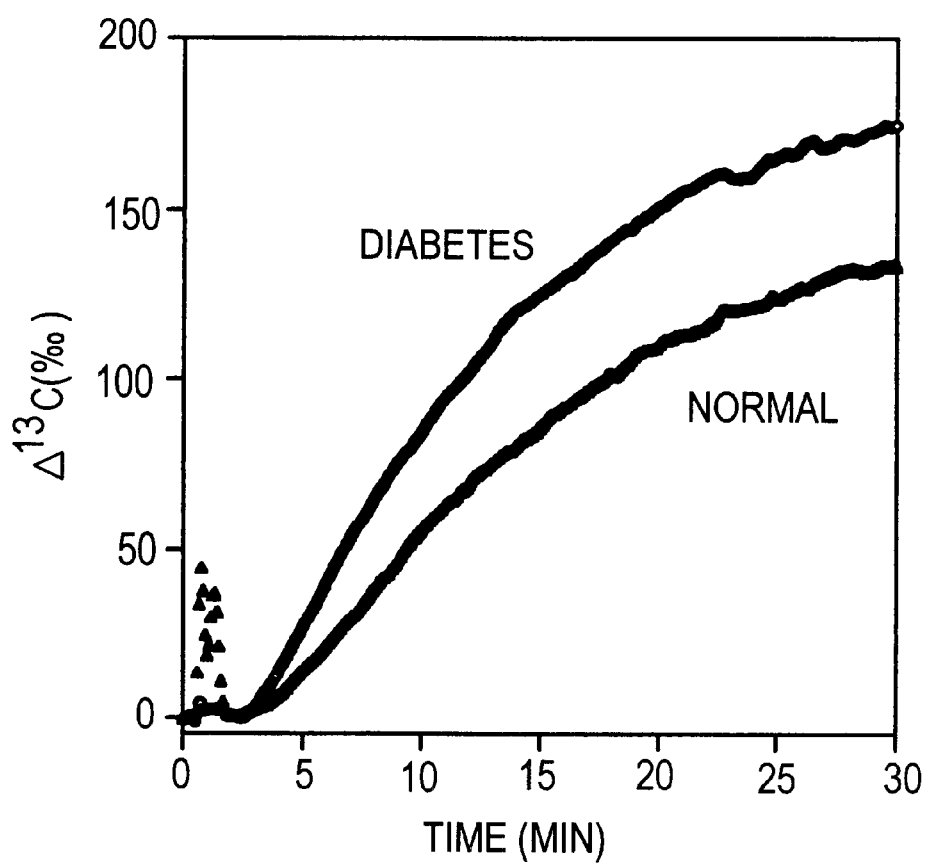
FIG. 29 shows the increase of $^{13}CO_2$ in exhalation after administration of 1,1,1-$^{13}$C-trioctanoin.

In both the normal and the diabetic rats, $\Delta^{13}C$ values (‰) continued increasing up to 30 min after the administration of $1,1,1\text{-}^{13}C$-trioctanoin (FIG. 29).

The $\Delta^{13}C$ value (‰) at 20 min after the administration was 150.72±22.48‰ in the diabetic rats, while the corresponding value was 110.16±16.08‰ in the normal rats. Thus, the value in the diabetic rats was significantly (p<0.05 (ANOVA with Fischer LSD)) higher than that in the normal rats.

Accordingly, it is possible to diagnose diabetes from the $\Delta^{13}C$ value (‰) at a specific time after administration of $1,1,1\text{-}^{13}C$-trioctanoin. With this test, it is possible to diagnose even light diabetes which shows a normal blood sugar level at the time of fasting.

EXAMPLE 34

$1,1,1\text{-}^{13}C$-Triacetin Test $1,1,1\text{-}^{13}C$-triacetin emulsified with Tween 20 (0.4%) and physiological saline was administered to normal rats (9-week-old; fasting blood sugar level 67.7±6.8 mg/dl; n=3) and diabetic rats (9-week-old; casual blood sugar level 332±44.2 mg/dl; fasting blood sugar level 80.3±15.0 mg/dl; n=4) from the femoral vein at a dose of 10 mg/kg. Then, degrees of increase of $^{13}C$ levels in exhaled $CO_2$ ($\Delta^{13}C$ (‰) were measured according to the method described in Example 1.

Figure 30:
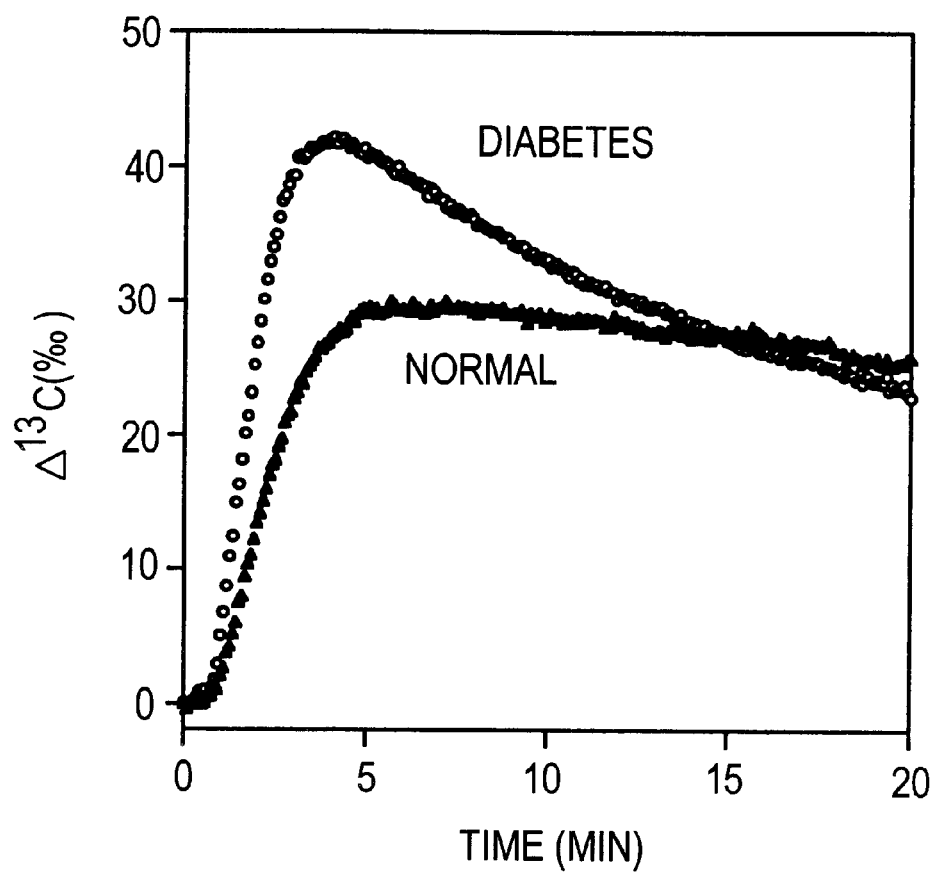
FIG. 30 shows the increase of $^{13}CO_2$ in exhalation after administration of 1,1,1-$^{13}$C-triacetin.

In the normal rats, $\Delta^{13}C$ values (‰) continued increasing up to 20 min after the administration of $1,1,1\text{-}^{13}C$-triacetin. In the diabetic rats, $\Delta^{13}C$ values (‰) increased sharply up to about 8 min after the administration, but thereafter decreased gradually up to 20 min (FIG. 30).

The $\Delta^{13}C$ value (‰) at 4 min after the administration was 41.97±2.79‰ in the diabetic rats, while the corresponding value was 27.29±2.31‰ in the normal rats. Thus, the value in the diabetic rats was very significantly (p<0.01 (ANOVA with Fischer LSD)) higher than that in the normal rats.

The slope from 6 to 10 min after the administration was −6.26±1.50‰/4 min in the diabetic rats, while the corresponding slope was −0.83±0.90‰/4 min in the normal rats. Thus, the slope in the diabetic rats was very significantly (p<0.01 (ANOVA with Fischer LSD)) smaller than that in the normal rats.

Accordingly, it is possible to diagnose diabetes from the $\Delta^{13}C$ value (‰) at a specific time after administration of $1,1,1\text{-}^{13}C$-triacetin or from the slope of increase of $\Delta^{13}C$ values (‰) after the administration. With this test, it is possible to diagnose even light diabetes which shows a normal blood sugar level at the time of fasting.

EXAMPLE 35

$2\text{-}^{13}C$-Glycerol Breath Test $2\text{-}^{13}C$-glycerol (purchased from CIL) dissolved in physiological saline was administered to normal rats (9-week-old; fasting blood sugar level 70.3±4.1 mg/dl; n=4) and diabetic rats (9-week-old; casual blood sugar level 440±18.0 mg/dl; fasting blood sugar level 83±9.3 mg/dl; n=3) from the femoral vein at a dose of 50 mg/kg. Then, degrees of increase of $^{13}C$ levels in exhaled $CO_2$ ($\Delta^{13}C$ (‰)) were measured according to the method described in Example 1.

Figure 31:
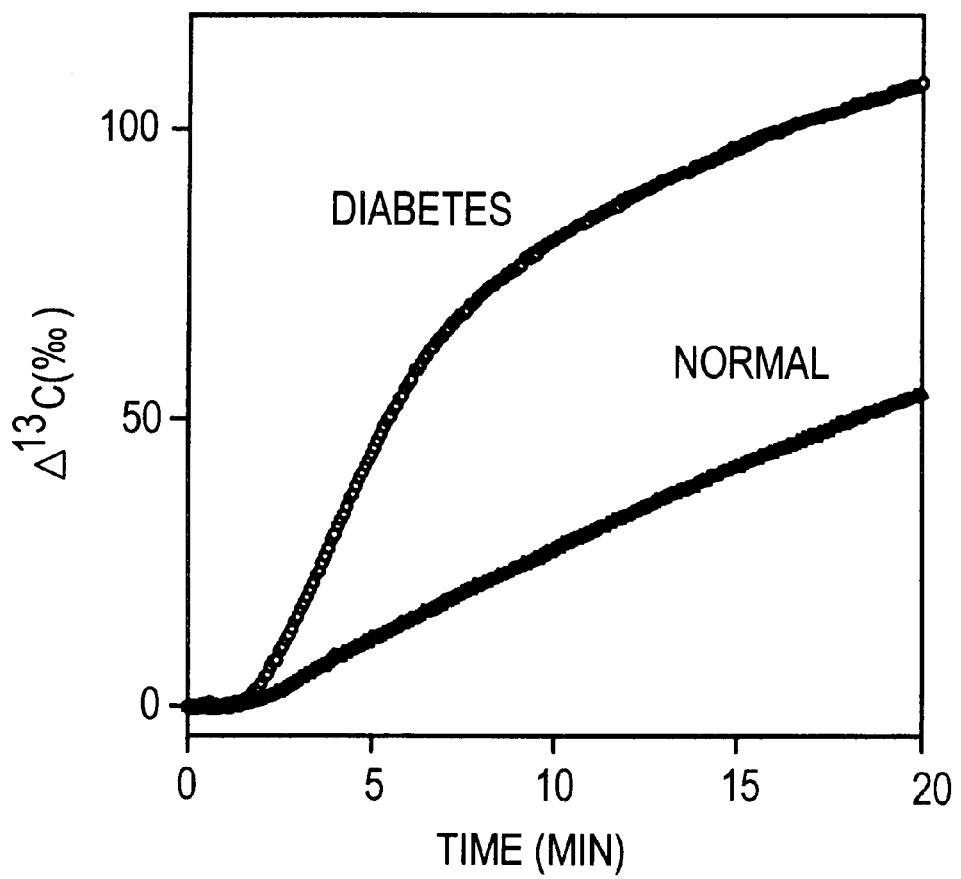
FIG. 31 shows the increase of $^{13}CO_2$ in exhalation after administration of 2-$^{13}$C-glycerol.

In the normal rats, $\Delta^{13}C$ values (‰) continued increasing gradually up to 20 min after the administration of $2\text{-}^{13}C$-glycerol, and thereafter remained at an almost constant level. In the diabetic rats, $\Delta^{13}C$ values (‰) increased sharply up to about 8 min after the administration, and thereafter increased gradually up to 20 min (FIG. 31).

The $\Delta^{13}C$ value (‰) at 20 min after the administration was 112.44±5.12‰ in the diabetic rats, while the corresponding value was 54.77±4.23‰ in the normal rats. Thus, the value in the diabetic rats was very significantly (p<0.0001 (ANOVA with Fischer LSD)) higher than that in the normal rats.

The slope from 2 to 7 min after the administration was 62.72±3.22‰/5 min in the diabetic rats, while the corresponding slope was 16.99±1.61‰/5 min in the normal rats. Thus, the slope in the diabetic rats was very significantly (p<0.0001 (ANOVA with Fischer LSD)) greater than that in the normal rats.

Accordingly, it is possible to diagnose diabetes from the $\Delta^{13}C$ value (‰) at a specific time after administration of $2\text{-}^{13}C$-glycerol or the slope of increase of $\Delta^{13}C$ values (‰) after the administration. With this test, it is possible to diagnose even light diabetes which shows a normal blood sugar level at the time of fasting.

EXAMPLE 36

N,N-Dimethyl-$^{13}C$-Aminopyrin Breath Test

N,N-dimethyl-$^{13}C$-aminopyrin (purchased from ICON) dissolved in physiological saline was administered to normal rats (8-week-old; fasting blood sugar level 68.8±4.0 mg/dl; n=4) and diabetic rats (8-week-old; casual blood sugar level 414.5±29.9 mg/dl; fasting blood sugar level 94.8±10.0 mg/dl; n=4) from the femoral vein at a dose of 40 mg/kg. Then, degrees of increase of $^{13}C$ levels in exhaled $CO_2$ ($\Delta^{13}C$ (‰)) were measured according to the method described in Example 1.

Figure 32:
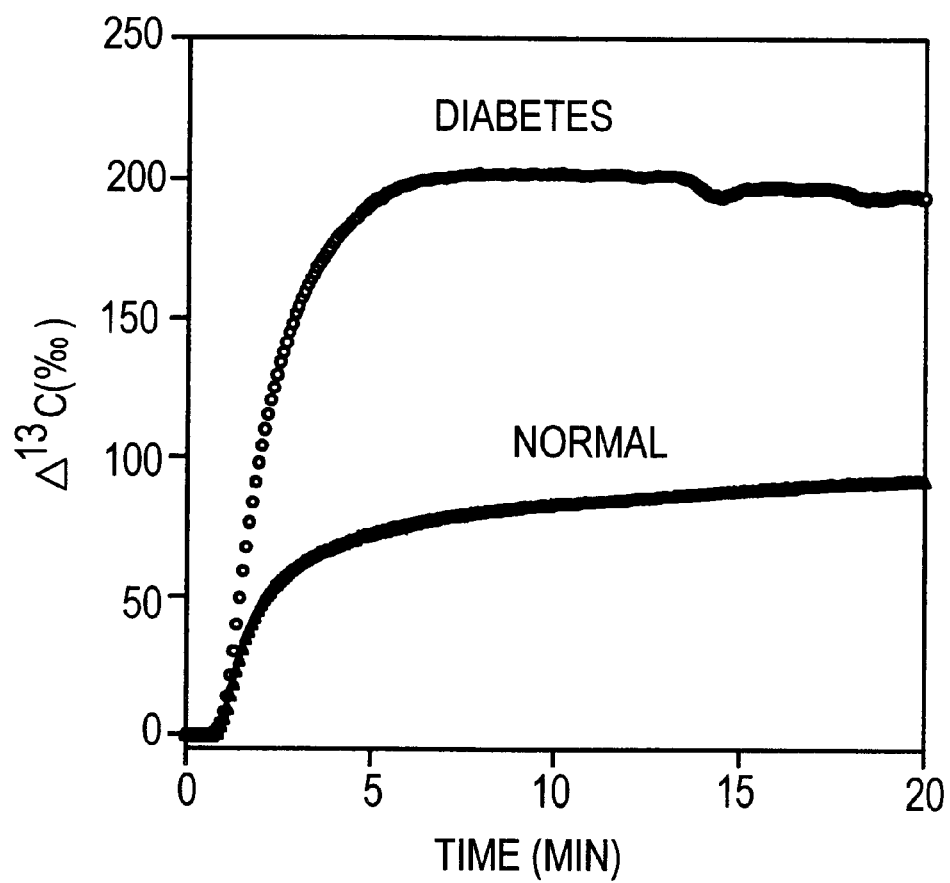
FIG. 32 shows the increase of $^{13}CO_2$ in exhalation after administration of N,N-dimethyl-$^{13}$C-aminopyrin.

In the normal rats, $\Delta^{13}C$ values (‰) increased sharply up to about 3 min after the administration of N,N-dimethyl-$^{13}C$-aminopyrin, and thereafter increased gradually up to 20 min. In the diabetic rats, $\Delta^{13}C$ values (‰) increased sharply up to about 5 min after the administration, and thereafter remained at an almost constant level up to 20 min (FIG. 32).

The $\Delta^{13}C$ value (‰) at 20 min after the administration was 193.62±22.21‰ in the diabetic rats, while the corresponding value was 92.2±12.64‰ in the normal rats. Thus, the value in the diabetic rats was very significantly (p<0.001 (ANOVA with Fischer LSD)) higher than that in the normal rats.

The slope from 1 to 2 min after the administration was 95.68±16.33‰/min in the diabetic rats, while the corresponding slope was 41.16±8.89‰/min in the normal rats. Thus, the slope in the diabetic rats was very significantly ($p<0.01$ (ANOVA with Fischer LSD)) greater than that in the normal rats.

Accordingly, it is possible to diagnose diabetes from the $\Delta^{13}C$ value (‰) at a specific time after administration of N,N-dimethyl-$^{13}C$-aminopyrin or the slope of increase of $\Delta^{13}C$ values (‰) after the administration. With this test, it is possible to diagnose even light diabetes which shows a normal blood sugar level at the time of fasting.

EXAMPLE 37

Ethoxy-1-$^{13}C$-Phenacetin Breath Test

Ethoxy-1-$^{13}C$-phenacetin (purchased from ICON) suspended in 0.5% aqueous solution of carboxymethylcellulose was administered orally to normal rats (9-week-old; fasting blood sugar level 72±8.9 mg/dl; n=4) and diabetic rats (9-week-old; casual blood sugar level 504.7±55.0 mg/dl; fasting blood sugar level 101.7±3.3 mg/dl; n=3) at a dose of 90 mg/kg. Then, degrees of increase of $^{13}C$ levels in exhaled $CO_2$ ($\Delta^{13}C$ (‰)) were measured according to the method described in Example 1.

Figure 33:
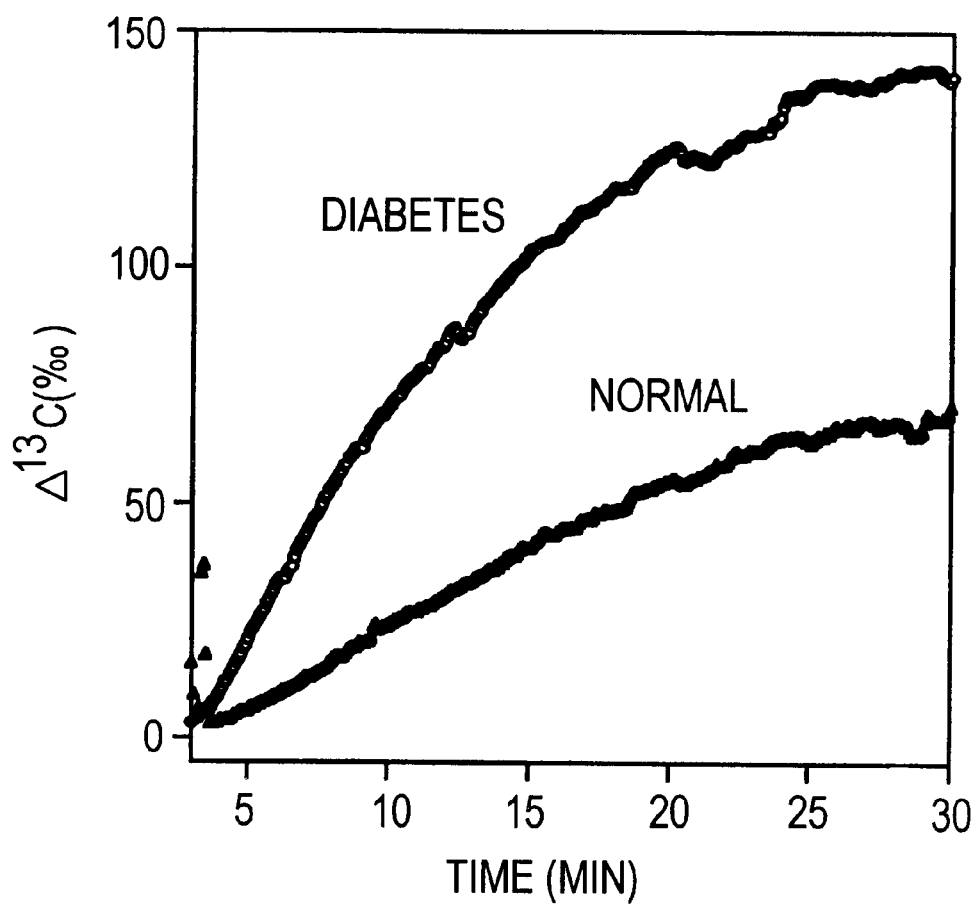
FIG. 33 shows the increase of $^{13}CO_2$ in exhalation after administration of ethoxy-1-$^{13}$C-phenacetin.

In both the normal and the diabetic rats, $\Delta^{13}C$ values (‰) continued increasing up to 30 min after the administration of ethoxy-1-$^{13}C$-phenacetin (FIG. 33).

The $\Delta^{13}C$ value (‰) at 30 min after the administration was 119.85±13.87‰ in the diabetic rats, while the corresponding value was 70.99±12.34‰ in the normal rats. Thus, the value in the diabetic rats was very significantly ($p<0.01$ (ANOVA with Fischer LSD)) higher than that in the normal rats.

The slope from 10 to 15 min after the administration was 30.88±5.62‰/5 min in the diabetic rats, while the corresponding slope was 16.3±4.47‰/5 min in the normal rats. Thus, the slope in the diabetic rats was significantly ($p<0.05$ (ANOVA with Fischer LSD)) greater than that in the normal rats.

Accordingly, it is possible to diagnose diabetes from the $\Delta^{13}C$ value (‰) at a specific time after administration of ethoxy-1-$^{13}C$-phenacetin or the slope of increase of $\Delta^{13}C$ values (‰) after the administration. With this test, it is possible to diagnose even light diabetes which shows a normal blood sugar level at the time of fasting.

EXAMPLE 38

Ethoxy-$^{13}C$-Methacetin Breath Test

Ethoxy-$^{13}C$-methacetin (purchased from CIL) suspended in 0.5% aqueous solution of carboxymethylcellulose was administered orally to normal rats (8-week-old; fasting blood sugar level 86±2.9 mg/dl; n=4) and diabetic rats (8-week-old; casual blood sugar level 418.5±24.9 mg/dl; fasting blood sugar level 90.3±6.6 mg/dl; n=4) at a dose of 90 mg/kg. Then, degrees of increase of $^{13}C$ levels in exhaled $CO_2$ ($\Delta^{13}C$ (‰)) were measured according to the method described in Example 1.

The slope from 12 to 17 min after the administration of ethoxy-$^{13}C$-methacetin was −8.40±7.67‰/5 min in the diabetic rats, while the corresponding slope was 16.05±7.71‰/5 min in the normal rats. Thus, the slope in the diabetic rats was very significantly ($p<0.01$ (ANOVA with Fischer LSD)) smaller than that in the normal rats.

Accordingly, it is possible to diagnose diabetes from the slope of increase of $\Delta^{13}C$ values (‰) after administration of ethoxy-$^{13}C$-methacetin. With this test, it is possible to diagnose even light diabetes which shows a normal blood sugar level at the time of fasting.

FORMULATION EXAMPLE 1

Injection 10 parts by weight of 1-$^{13}C$-galactose was dissolved in 90 parts by weight of physiological saline and sterilized by filtration with a Millipore filter. The filtrate was put into a vial and sealed to give an injection.

FORMULATION EXAMPLE 2

Internal Liquid Agent 10 parts by weight of 1-$^{13}C$-fructose was dissolved in 90 parts by weight of deionized and distilled water (DDW) and sterilized by filtration with a Millipore filter. The filtrate was put into a vial and sealed to give an internal liquid agent.

FORMULATION EXAMPLE 3

Injection 10 parts by weight of 1-$^{13}C$-isoleucine was dissolved in 90 parts by weight of physiological saline and sterilized by filtration with a Millipore filter. The filtrate was put into a vial and sealed to give an injection.

FORMULATION EXAMPLE 4

Internal Liquid Agent 10 parts by weight of 1-$^{13}C$-alanine was dissolved in 90 parts by weight of DDW and sterilized by filtration with a Millipore filter. The filtrate was put into a vial and sealed to give an internal liquid agent.

FORMULATION EXAMPLE 5

Injection 10 parts by weight of 3-$^{13}C$-sodium lactate was dissolved in 90 parts by weight of physiological saline and sterilized by filtration with a Millipore filter. The filtrate was put into a vial and sealed to give an injection.

FORMULATION EXAMPLE 6

Internal Liquid Agent 10 parts by weight of 1,6-$^{13}C$-citric acid was dissolved in 90 parts by weight of DDW and sterilized by filtration with a Millipore filter. The filtrate was put into a vial and sealed to give an internal liquid agent.

FORMULATION EXAMPLE 7

Injection 10 parts by weight of 1-$^{13}C$-oleic acid, 89 parts by weight of physiological saline and 1 part by weight of Polysorbate 80 (all sterilized in advance) were mixed aseptically and emulsified with a ultrasonic homogenizer. The resultant emulsion was put into a vial and sealed to give an injection.

FORMULATION EXAMPLE 8

Internal Liquid Agent 10 parts by weight of 1-$^{13}C$-acetic acid was dissolved in 90 parts by weight of DDW and sterilized by filtration with a Millipore filter. The filtrate was put into a vial and sealed to give an internal liquid agent.

FORMULATION EXAMPLE 9

Injection 10 parts by weight of 1,1,1-$^{13}$C-trioctanoin, 89 parts by weight of physiological saline and 1 part by weight of Polysorbate 80 (all sterilized in advance) were mixed aseptically and emulsified with a ultrasonic homogenizer. The resultant emulsion was put into a vial and sealed to give an injection.

FORMULATION EXAMPLE 10

Internal Liquid Agent 10 parts by weight of 1,1,1-$^{13}$C-trioctanoin, 89 parts by weight of DDW and 1 part by weight of Tween 80 (all sterilized in advance) were mixed aseptically and emulsified with a ultrasound homogenizer. The resultant emulsion was put into a vial and sealed to give an internal liquid agent.

FORMULATION EXAMPLE 11

Injection 10 parts by weight of 2-$^{13}$C-glycerol was dissolved in 90 parts by weight of physiological saline and sterilized by filtration with a millipore filter. The filtrate was put into a vial and sealed to give an injection.

FORMULATION EXAMPLE 12

Internal Liquid Agent 10 parts by weight of 2-$^{13}$C-glycerol was dissolved in 90 parts by weight of DDW and sterilized by filtration with a Millipore filter. The filtrate was put into a vial and sealed to give an internal liquid agent.

FORMULATION EXAMPLE 13

Injection 10 parts by weight of N,N-dimethyl-$^{13}$C-aminopyrin was dissolved in 90 parts by weight of physiological saline and sterilized by filtration with a Millipore filter. The filtrate was put into a vial and sealed to give an injection.

FORMULATION EXAMPLE 14

Internal Liquid Agent 10 parts by weight of N,N-dimethyl-$^{13}$C-aminopyrin was dissolved in 90 parts by weight of DDW and sterilized by filtration with a Millipore filter. The filtrate was put into a vial and sealed to give an internal liquid agent.

What is claimed is:

1. A pharmaceutical preparation comprising lactic acid labeled with $^{13}$C at one or more positions as a diagnostic agent, wherein said diagnostic agent is present with a pharmaceutically acceptable carrier suitable for parenteral or oral administration.

2. A method for diagnosing diabetes, comprising the steps of:

administering to a subject a lactic acid labeled with $^{13}$C at one or more positions;

measuring $^{13}$C levels in the exhaled $CO_2$ for a specific period of time; and comparing the increase of $^{13}$C levels in the exhaled $CO_2$ of the test subject to the corresponding increase in $^{13}$C levels in the exhaled $CO_2$ in normal subjects.

* * * * *